(12) United States Patent
Paas et al.

(10) Patent No.: US 9,073,990 B2
(45) Date of Patent: Jul. 7, 2015

(54) PROTEASE-ACTIVATABLE PORE-FORMING POLYPEPTIDES

(75) Inventors: Yoav Paas, Nes Ziona (IL); Ilya Pittel, Brookline, MA (US); Uri Nir, Moshav Gimzo (IL); Barak Ben-David, Karney Shomron (IL)

(73) Assignee: Bar-Ilan University, Ramat-Gan (IL)

( * ) Notice: Subject to any disclaimer, the term of this patent is extended or adjusted under 35 U.S.C. 154(b) by 0 days.

(21) Appl. No.: 13/261,466

(22) PCT Filed: Apr. 4, 2011

(86) PCT No.: PCT/IB2011/051433
§ 371 (c)(1),
(2), (4) Date: Oct. 4, 2012

(87) PCT Pub. No.: WO2011/125015
PCT Pub. Date: Oct. 13, 2011

(65) Prior Publication Data
US 2013/0121915 A1    May 16, 2013

Related U.S. Application Data

(60) Provisional application No. 61/282,809, filed on Apr. 5, 2010.

(51) Int. Cl.
| | | |
|---|---|---|
| *C07K 14/21* | (2006.01) | |
| *A61K 47/42* | (2006.01) | |
| *C07K 14/245* | (2006.01) | |
| *A61K 47/48* | (2006.01) | |
| *B82Y 5/00* | (2011.01) | |
| *C07K 14/195* | (2006.01) | |
| *A61K 38/00* | (2006.01) | |

(52) U.S. Cl.
CPC ............... *C07K 14/245* (2013.01); *A61K 38/00* (2013.01); *A61K 47/48338* (2013.01); *B82Y 5/00* (2013.01); *C07K 14/195* (2013.01); *A61K 47/42* (2013.01); *C07K 14/21* (2013.01)

(58) Field of Classification Search
CPC ............... C07K 14/21; C07K 2319/35; C07K 2319/00; C07K 2319/035; A61K 38/00; A61K 47/42; G01N 33/5432; G01N 33/574
See application file for complete search history.

(56) References Cited

U.S. PATENT DOCUMENTS

| | | | |
|---|---|---|---|
| 5,939,096 | A | 8/1999 | Clerc et al. |
| 2004/0180094 | A1 | 9/2004 | Joyce |
| 2005/0272677 | A1 | 12/2005 | Friesen et al. |
| 2006/0210549 | A1 | 9/2006 | Srivastava et al. |
| 2007/0140972 | A1* | 6/2007 | Zhu et al. ............... 424/9.34 |
| 2009/0016988 | A1 | 1/2009 | Buckley |

FOREIGN PATENT DOCUMENTS

| | | |
|---|---|---|
| WO | WO 2005/069750 | 8/2005 |
| WO | WO 2011/125015 | 10/2011 |

OTHER PUBLICATIONS

Biswas et al. Structural insight into OprD substrate specificity. Nat Struct Mol Biol. Nov. 2007;14(11):1108-9.*
Black et al. Primary sequence of the *Escherichia coli* fadL gene encoding an outer membrane protein required for long-chain fatty acid transport. J. Bacteriol. 1991, 173(2):435.*
Kwon et al. Highly efficient protein expression and purification using bacterial hemoglobin fusion vector. Plasmid 53 (2005) 274-282.*
Zeng et al. Matrix Metalloproteinase-7 Expression in Colorectal Cancer Liver Metastases: Evidence for Involvement of MMP-7 Activation in Human Cancer Metastases. Clin Cancer Res 2002;8:144-148.*
Israelachvili et al. Molecular layering of water at surfaces and origin of repulsive hydration forces. Nature 1983. 306, 249-250.*
Biswas et al. Structural insight into OprD substrate specificity. Nat Struct Mol Biol. Nov. 2007;14(11):1108-9 and supplementary data.*
Ochs et al. Negative Regulation of the *Pseudomonas aeruginosa* Outer Membrane Porin OprD Selective for Imipenem and Basic Amino Acids. Antimicrob Agents Chemother. May 1999;43(5):1085-90.*
Vargo-Gogola et al. "Identification of Novel Matrix Metalloproteinase-7 (Matrilysin) Cleavage Sites in Murine and Human Fas Ligand", Archives of Biochemistry and Biophysics, 408: 155-161, 2002.
Communication Relating to the Results of the Partial International Search Dated Aug. 22, 2011 From the International Searching Authority Re: Application No. PCT/IB2011/051433.
International Preliminary Report on Patentability Dated Oct. 18, 2012 From the International Bureau of WIPO Re. Application No. PCT/ID2011/051433.
International Search Report and the Written Opinion Dated Dec. 19, 2011 From the International Searching Authority Re: Application No. PCT/IB2011/051433.
Banerjee et al. "Release of Liposomal Contents by Cell-Secreted Matrix Metalloproteinase-9", Bioconjugate Chemistry, 20: 1332-1339, 2009.
Bayley "Pore-Forming Proteins With Built-In Triggers and Switches", Bioorganic Chemistry, XP002655296, 23(4): 340-354, 1995.
Bayley "Pore-Forming Proteins With Built-in Triggers and Switches", Bioorganic Chemistry, XP002655296, 23(4): 340-354, Dec. 1995. p. 348, Para 1.

(Continued)

*Primary Examiner* — Karlheinz R Skowronek
*Assistant Examiner* — Jia-Hai Lee

(57) ABSTRACT

An isolated pore-forming polypeptide is disclosed which comprises a naturally-occurring plugging module and a naturally-occurring pore domain, wherein at least one amino acid of the pore-forming polypeptide is mutated to generate a protease cleavage site, serving to at least partially remove the plugging module from the pore domain. The pore forming polypeptides may be inserted into an encapsulating particle and positioned such that it is capable of forming a pore through the lipid layer of the particle in a presence of the protease.

14 Claims, 11 Drawing Sheets
(8 of 11 Drawing Sheet(s) Filed in Color)

(56) References Cited

OTHER PUBLICATIONS

Elegbede et al. "Mechanistic Studies of the Triggered Release of Liposomal Contents by Matrix Metalloproteinase-9", Journal of the American Chemical Society, JACS, 130: 10633-10642, 2008.
Huang et al. "Membrane Topology and Site-Specific Mutagenesis of *Pseudomonas aeruginosa* Porin OprD", Molecular Microbiology, XP002655294, 16(5): 931-941, Jun. 1995.
Koebnik et al. "Insertion Derivatives Containing Segments of Up to 16 Amino Acids Identify Surface- and Periplasm-Exposed Regions of the FhuA Outer Membrane Receptor of *Escherichia coli* K-12", Journal of Bacteriology, XP002655295, 175(3): 826-839, Feb. 1993.
Lahlil et al. "The Potential Anti-Tumorigenic and Anti-Metastatic Side of the Proprotein Convertases Inhibitors", Recent Patents in Anti-Cancer Drug Discovery, XP055012601, 4(1): 83-91, Jan. 1, 2009. Abstract, p. 83, 1-h Col., Para 1.
Meers "Enzyme-Activated Targeting of Liposomes", Advanced Drug Delivery Reviews, 53: 265-272, 2001.
Panchal et al. "Tumor Protease-Activated, Pore-Forming Toxins From a Combinatorial Library", Nature Biotechnology, 14: 852-856, Jul. 1996.
Russo et al. "Reversible Permeabilization of Plasma Membranes With an Engineered Switchable Pore", Nature Biotechnology, 15: 278-282, Mar. 1997.
Soreide et al. "Trypsin in Colorectal Cancer: Molecular Biological Mechanisms of Proliferation, Invasion, and Metastasis", Journal of Pathology, XP055012602, 209(2): 147-156, Jun. 1, 2006. Abstract.
Turk et al. "Determination of Protease Cleavage Site Motifs Using Mixture-Based Oriented Peptide Libraries", Nature Biotechnology, 19: 661-667, Jul. 2001.
Yoshihara et al. "Calcium Ion-Mediated Opening of the Channel Gate in the *Pseudomonas aeruginosa* Porin", Biochemical and Biophysical Research Communications, XP002655297, 194(3): 1460-1465, Aug. 16, 1993.
Yoshihara et al. "Separation of Gate- and Channel-Forming Domains in the Pore-Forming Protein of the Outer Membrane of *Pseudomonas aeruginosa*", FEBS Letters, XP002655298, 306(1): 5-8, Jul. 13, 1992. Figs. 1b, 2a.

\* cited by examiner

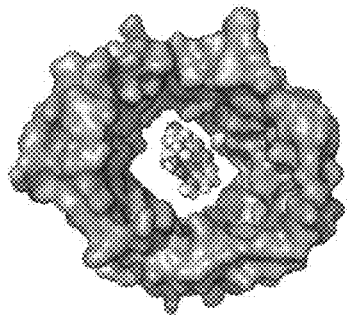

```
OprD_Model    FVSDQAEAKGFIEDSSLDLLLRNYYFNRDGKSGSGDRVDWTQGFITTYESGFTQGTVGFG  60
OprD_Cut      FVSDQAEAKGFIEDSSLDLLLRNYYFNRDGKSGSGDRVDWTQGFITTYESGFTQGTVGFG  60
              ************************************************************

OprD_Model    VDAFGYLGLKLDGTSDKTGTGNLPVMNDGKPRDDYSRAGGAVKVRISKTMLKWGEMQPTA  120
OprD_Cut      VDAFGYLGLKLDGTSDKTGTGNLPVMNDGKPRDDYSRAGGAVKVRISKTMLKWGEM----  117
              ******************************************************

OprD_Model    PVFAAGGSRLFPQTATGFQLQSSEFEGLDLEAGHFTEGKEPTTVKSRGELYATYAGETAK  180
OprD_Cut      ----TATGFQLQSSEFEGLDLEAGHFTEGKEPTTVKSRG---------------------  151
                  ***********************************

OprD_Model    SADFIGGRYAITDNLSASLYGAELEDIYRQYYLNSNYTIPLASDQSLGFDFNIYRTNDEG  240
OprD_Cut      SADFIGGRYAITDNLSASLYGAELEDIYRQYYLNSNYTIPLASDQSLGFDFNIYRTNDEG  211
              ************************************************************

OprD_Model    KAKAGDISNTTWSLAAAYTLDAHTFTLAYQKVHGDQPFDYIGFGRNGSGAGGDSIFLANS  300
OprD_Cut      KAKAGDISNTTWSLAAAYTLDAHTFTLAYQKVHGDQP-----------------------  248
              ************************************

OprD_Model    VQYSDFNGPGEKSWQARYDLNLASYGVPGLTFMVRYINGKDIDGTKMSDNNVGYKNYGYG  360
OprD_Cut      ----FNGPGEKSWQARYDLNLASYGVPGLTFMVRYINGKDIDGTK---------------  289
                  ****************************************

OprD_Model    EDGKHHETNLEAKYVQSGPAKDLSFRIRQAWHRANADQGEGDQNEFRLIVDYPLSIL  418
OprD_Cut      EDGKHHETNLEAKYVQSGPAKDLSFRIRQAWHRANADQGEGDQNEFRLIVDYPLSIL  347
              ********************************************************
```

PROTEASE-ACTIVATABLE PORE-FORMING POLYPEPTIDES

RELATED APPLICATIONS

This application is a National Phase of PCT Patent Application No. PCT/IB2011/051433 having International filing date of Apr. 4, 2011, which claims the benefit of priority under 35 USC §119(e) of U.S. Provisional Patent Application No. 61/282,809 filed on Apr. 5, 2010. The contents of the above applications are all incorporated by reference as if fully set forth herein in their entirety.

FIELD AND BACKGROUND OF THE INVENTION

The present invention, in some embodiments thereof, relates to pore-forming polypeptides that are naturally plugged and are engineered to open by the action of proteases. The plugged pore-forming polypeptides may be incorporated at the surface of encapsulating particles such that they generate pores in the particles only upon exposure to specific proteases. Opening of the pores releases the content of the encapsulating particle.

Cancer is currently the second leading cause of death in the United States. 85% of cancer patients have solid tumors and 50% of those patients die as a result of malignant disease. Local control of the tumor is particularly difficult in the cervix, colon, ovarian, pancreas, and brain. There is hence an urgent and currently unmet need to improve eradication of primary solid tumors and solid metastases.

Most chemotherapeutic drugs act on both normal as well as cancerous tissues. As such, one of the challenges in treating cancerous tumors with chemotherapy is maximizing the killing of cancer cells while minimizing the harming of healthy tissue. Depending on the administration route (e.g., intravenous) and nature of the drug (e.g., its physical and pharmacokinetic properties), oftentimes only a small fraction of the dose reaches the target cells; the remaining amount of drug acts on other tissues or is rapidly eliminated.

Standard chemotherapeutic drugs (e.g., Doxorubicin, Camptothecin, Paclitaxel, and Palatinate) are usually injected systemically to the patient and act by preventing the proliferation of the cancer cells. These drugs must be administered at low doses since they are very aggressive and have many harsh side effects. Doxorubicin, for example, has limited specificity, killing all fast replicating cells, by: intercalating into the DNA to prevent its unwinding by Topoisomerase II and inhibiting macromolecule synthesis. As such, many healthy cells including white blood cells, gastrointestinal cells, and hair follicles are also susceptible to the effects of the drug, leading to pathophysiological conditions such as neutropenia, stomatitis, and alopecia. Some new drug treatments utilize chemoprotective agents to help prevent side effects by protecting healthy cells against the drug's toxicity. Other treatments reduce side effects by improving the chemistry of the drug, while some improve the drug-delivery to the cancer cells.

To improve delivery efficiency and reduce toxicity to non-target cells, various strategies have been used to deliver drugs to specific sites in the human body. Tumor cells are often characterized by a specific expression pattern of membrane associated proteins such as receptors, membrane transport systems or adhesion molecules. Provided that these structures are accessible from the extracellular milieu, such properties can be exploited for an active targeting of diseased cells and tissues using specific effector molecules. The concept of active targeting has the potential to combine the advantage of an increased therapeutic efficacy with a reduced risk for adverse side-effects in non-diseased tissues. With the arrival of genetic engineering technologies, which made it possible to design chimeric mouse-human monoclonal antibodies or recombinant peptidic receptor ligands, the clinical use of these active tumor targeting strategies has become reality.

Various carriers have been explored including liposomal vectors, micelles, carbon nanotubes, polymeric nanoparticles, polymer conjugates, hyalronan-shelled bodies, and lipidic cubic phases for increasing the delivery of a chemotherapeutic drug to a target site.

The use of liposomes is particularly advantageous since its pharmacokinetic properties can be modulated by specific modifications of the liposome surface. Besides direct chemical modifications of the phospholipid headgroups (such as the introduction of surface charges or hydrophilic groups, conjugation of proteins, peptides or other macromolecules to the liposome surface can be achieved. Chemical conjugation techniques provide thereby a stable link between the liposomal phospholipids and a specific targeting vector. The availability of pegylated liposomes made the development of vector-conjugated liposomes possible since the unique properties of these long-circulating liposomes can be combined with those of a targeting vector of choice within one preparation.

Triggered release of drugs and labeled molecules from liposomes has been recognized to be an attractive therapeutic approach. In this approach of drug delivery, the drug delivery vehicles do not release contents until the vehicle's membranes are destabilized by the external agents (trigger). The trigger can be a change in mechanical stress, metal ions, or enzymes such as elastase, alkaline phosphatase, trypsin and phospholipase $A_2$. Conformational changes of peptides, induced by the change in pH, have also been used to facilitate the content release from liposomes.

U.S. Patent Application 20060210549 teaches triple helix trigger peptides which destabilize a liposome preparation on contact with a protease enzyme. These helical peptides do not create pores per se and further are devoid of plugging modules.

U.S. Patent Application 20090016988 teaches protease activated pore forming toxins as pharmaceutical agents for the treatment of cancer. The toxins are multisubunit proteins and do not comprise a naturally occurring plugging module.

U.S. Patent Application 20040180094 teaches protease-activated pore forming toxins as triggers for the release of agents inside an encapsulating vehicle. The toxins are multi-subunit proteins and do not comprise a naturally occurring plugging module.

Richard Lipkin [Science News, Cell Membrane Research Sep. 24, 1994] summarizes the review of Hagan Bayley [Bioorganic Chem 23, 340-354 (1995)] who teaches selective release of a drug from an encapsulating vehicle using a trigger which comprises a protease-activated multisubunit pore-forming toxin (alpha hemolysin). Bayley does not teach the use of pore-forming proteins which are not toxins and comprise naturally occurring plugging modules.

SUMMARY OF THE INVENTION

According to an aspect of some embodiments of the present invention there is provided an isolated pore-forming polypeptide comprising a naturally-occurring plugging module and a naturally-occurring pore domain, wherein at least one amino acid of the pore-forming polypeptide is mutated to generate a protease cleavage site, serving to at least partially remove the plugging module from the pore domain.

According to an aspect of some embodiments of the present invention there is provided an isolated polynucleotide encoding the isolated pore-forming polypeptide of the present invention.

According to an aspect of some embodiments of the present invention there is provided a nucleic acid construct comprising the polynucleotide of the present invention.

According to an aspect of some embodiments of the present invention there is provided a cell comprising the nucleic acid construct of the present invention.

According to an aspect of some embodiments of the present invention there is provided a composition of matter, comprising an encapsulating particle and the isolated polypeptide of the present invention, wherein the encapsulating particle comprises at least one lipid layer, and a compartment surrounded by the lipid layer, and further wherein the isolated polypeptide is positioned such that it is capable of forming a pore through the lipid layer in a presence of the protease.

According to an aspect of some embodiments of the present invention there is provided a pharmaceutical composition comprising the composition of matter of the present invention.

According to an aspect of some embodiments of the present invention there is provided a method of treating a disease associated with an up-regulation of a protease in a subject in need thereof, the method comprising administering to the subject a therapeutically effective amount of the composition of matter of the present invention to the subject, thereby treating the disease associated with the up-regulation of the protease.

According to some embodiments of the invention, the pore domain comprises a β barrel structure.

According to some embodiments of the invention, the isolated pore-forming polypeptide is a monomer.

According to some embodiments of the invention, the isolated pore-forming polypeptide comprises a Ton-B dependent receptor.

According to some embodiments of the invention, the Ton-B dependent receptor is selected from the group consisting of BtuB CirA, FatA, FcuT, FecA, FhuA FhuE, FepA, FptA, HemR, IrgA, IutA, PfeA, PupA and Tbp1.

According to some embodiments of the invention, the isolated pore-forming polypeptide comprises an amino acid sequence selected from the group consisting of SEQ ID NOs: 24-22778, 22780, 22782, 22784, 22786, 22788, 22790, 22792, 22794, 22796, 22798, 22800, 22802, 22804, 22806, 22808, 22810, 22812, 22814, 22816, 22820, 22822, 22824, 22826, 22828, 22830, 22832, 22834, 22836, 22838, 22840, 22842, 22844, 22846, 22848, 22850, 22852, 22854, 22858, 22860, 22862, 22864, 22866, 22868, 22870, 22872, 22874, 22876, 22878, 22880, 22882, 22884, 22886, 22888, 22892, 22894, 22898, 22900, 22902, 22904, 22906, 22908, 22910, 22912, 22914, 22916, 22918, 22920, 22922, 22924, 22926, 22928, 22930, 22932, 22934, 22936, 22938, 22940, 22942, 22944, 22946, 22948, 22950, 22952, 22954, 22956, 22958, 22960, 22962, 22986, 22964-22981.

According to some embodiments of the invention, the isolated pore-forming polypeptide is OprD.

According to some embodiments of the invention, when the pore-forming polypeptide is OprD the at least one mutated amino acid is positioned on Loop 3 (SEQ ID NO: 22990).

According to some embodiments of the invention, when the pore-forming polypeptide is OprD the at least one mutated amino acid is positioned in Loop 7 (SEQ ID NO: 22994).

According to some embodiments of the invention, when the pore-forming polypeptide is OprD the at least one mutated amino acid is positioned in Loop 3 and Loop 7 (SEQ ID NOs: 22990 and 22994).

According to some embodiments of the invention, when the pore-forming polypeptide is OprD the at least one mutated amino acid is positioned in Loop 8 (SEQ ID NO: 22995).

According to some embodiments of the invention, the protease cleavage site is cleaved by a protease associated with disease onset, or progression.

According to some embodiments of the invention, the protease cleavage site is cleaved by a protease associated with cancer onset, progression or metastasis.

According to some embodiments of the invention, the protease is selected from the group consisting of MMP-2, MMP-7, MMP-9 and MMP-14.

According to some embodiments of the invention, the protease is MMP-9.

According to some embodiments of the invention, the protease is MMP-2.

According to some embodiments of the invention, the protease is MMP-14.

According to some embodiments of the invention, the at least one mutated amino acid is situated on at least one loop of the pore-forming polypeptide.

According to some embodiments of the invention, the at least one mutated amino acid is situated on the plugging module of the pore-forming polypeptide.

According to some embodiments of the invention, a pore of the polypeptide is about 1.4-10 nm in diameter when fully unplugged.

According to some embodiments of the invention, a plugging of the pore with the plugging module of the pore-forming polypeptide prevents a passage of water.

According to some embodiments of the invention, the protease cleavage site is cleaved by a protease associated with cancer onset, progression and metastasis.

According to some embodiments of the invention, the protease is a member of a family selected from the group consisting of a matrix metalloproteinase (MMP) family, an elastase family, a plasminogen activator family and a fibroblast activation protein family.

According to some embodiments of the invention, the protease is a member of a matrix metalloproteinase (MMP) family.

According to some embodiments of the invention, the protease is selected from the group consisting of MMP-2, MMP-7, MMP-9 and MMP-14.

According to some embodiments of the invention, the protease is MMP-7.

According to some embodiments of the invention, the pore-forming polypeptide is FhuA or OprD.

According to some embodiments of the invention, the isolated pore-forming polypeptide comprises an amino acid sequence as set forth in SEQ ID NOs: 5 and 7.

According to some embodiments of the invention, the isolated pore-forming polypeptide further comprises an amino acid sequence which encodes an affinity tag.

According to some embodiments of the invention, the affinity tag is attached to an extracellular loop of the polypeptide.

According to some embodiments of the invention, the nucleic acid construct further comprises a cis-regulatory element.

According to some embodiments of the invention, the cis-regulatory element is a promoter.

According to some embodiments of the invention, the composition of matter further comprises a therapeutic agent in the compartment surrounded by the lipid layer.

According to some embodiments of the invention, the therapeutic agent is capable of passing through the pore in a presence of the protease.

According to some embodiments of the invention, the therapeutic agent is a small molecule having a molecular mass of less than 1000 Da.

According to some embodiments of the invention, the therapeutic agent is a polypeptide or a polynucleotide agent.

According to some embodiments of the invention, the composition of matter further comprises a diagnostic agent in the compartment surrounded by the lipid layer.

According to some embodiments of the invention, the lipid layer further comprises a targeting moiety.

According to some embodiments of the invention, the targeting moiety is selected from the group consisting of an antibody, an antibody fragment, a receptor ligand and an aptamer.

According to some embodiments of the invention, a size of the pore is configured to allow a passage of water into the encapsulating particle.

According to some embodiments of the invention, a size of the pore is configured to allow a passage of the therapeutic agent out of the encapsulating particle.

According to some embodiments of the invention, the encapsulating particle is a nanoparticle.

According to some embodiments of the invention, the encapsulating particle is a liposome.

According to some embodiments of the invention, the therapeutic agent is a chemotherapeutic agent.

According to some embodiments of the invention, the lipid layer comprises a hydrophilic polymer.

According to some embodiments of the invention, the hydrophilic polymer comprises at least one component selected from the group consisting of polyethylene glycol (PEG), polyelectrolyte poly(allylamine hydrochloride), polyacrylic acid, naturally-occurring glycosaminoglycans and naturally-occurring repeating disaccharides β1,3N-acetylglucosaminyl-β1,4 glucuronide, or naturally occurring hyaluronic acid.

According to some embodiments of the invention, the lipid layer comprises cholesterol.

According to some embodiments of the invention, the lipid layer comprises phospholipids.

According to some embodiments of the invention, the phospholipids are selected from the group consisting of glycerophospholipids, phosphatidylserine, phosphatidylethanolamine, phosphatidylcholine, phosphatidyl inositol and phosphatidyl glycerol.

According to some embodiments of the invention, the disease associated with an up-regulation of a protease is cancer.

According to some embodiments of the invention, the cancer is a solid tumor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
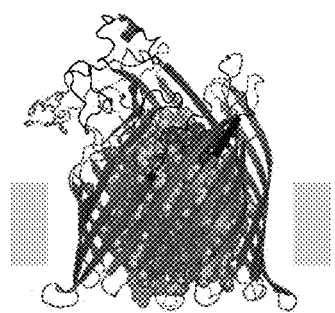
Figure 1F:
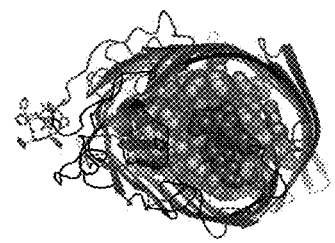
Figure 1B:
Figure 1G:
Figure 1C:
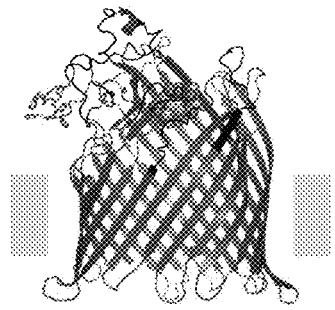
Figure 1H:
Figure 1D:
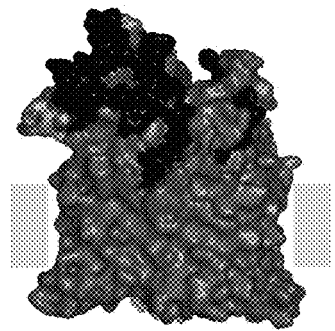
Figure 1I:
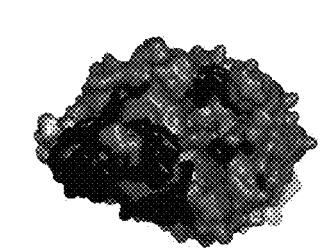
Figure 1E:
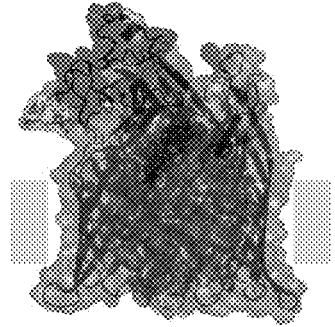
Figure 1J:
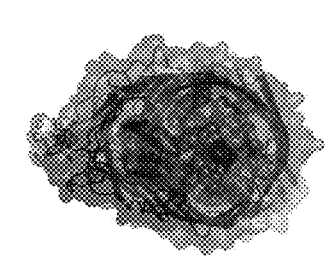

FIGS. 1A-J are cartoon representations of the (β-barrel FhuA$_{7/10}$-1 mutated protein. β strands are indicated as wide flat arrows; helices are indicated as wide flat coils; loop structures are thin spaghetti-like coils. The FhuA residues (161 to 725) are colored blue. Part of these residues form the transmembrane walls of the pore. MMP-7 cleavage sites are colored black in the barrel and dark gray in the orange colored cork. CPK colored sticks represent the hexa-histidine tag, where carbon and nitrogen atoms are shown in grey and blue colors, respectively. FIGS. 1A-E are side views where the FhuA$_{7/10}$-1 is situated perpendicular to the lipid membrane that is represented by gray rectangles. FIGS. 1F-J are top views looking down into the cytoplasm of the expressing mammalian cells (or the periplasmic space in gram-negative bacteria). FIGS. 1A and F, the cork domain (residues 19 to 160) is represented as spheres and is colored gold. FIGS. 1B and G: Space filling model of Doxorubicin inside the barrel of FhuA$_{7/10}$-1. The cork was removed to show the size of Doxorubicin relatively to the pore. FIGS. 1C and H: Space filling model of Ferrichrome from the crystal structure without the cork. FIGS. 1D and I: Connolly Surface shows the FhuA$_{7/10}$-1 where water or lipids contact it in all possible positions. FIGS. 1E and J: a transparent Connolly Surface of the β-barrel overlaid on FIGS. 1A and F. In all panels, atoms colored in grey, blue or red correspond to carbon, nitrogen and oxygen respectively. Note, Hydrogen atoms are not shown.

Figures 2A, 2B, 2C:
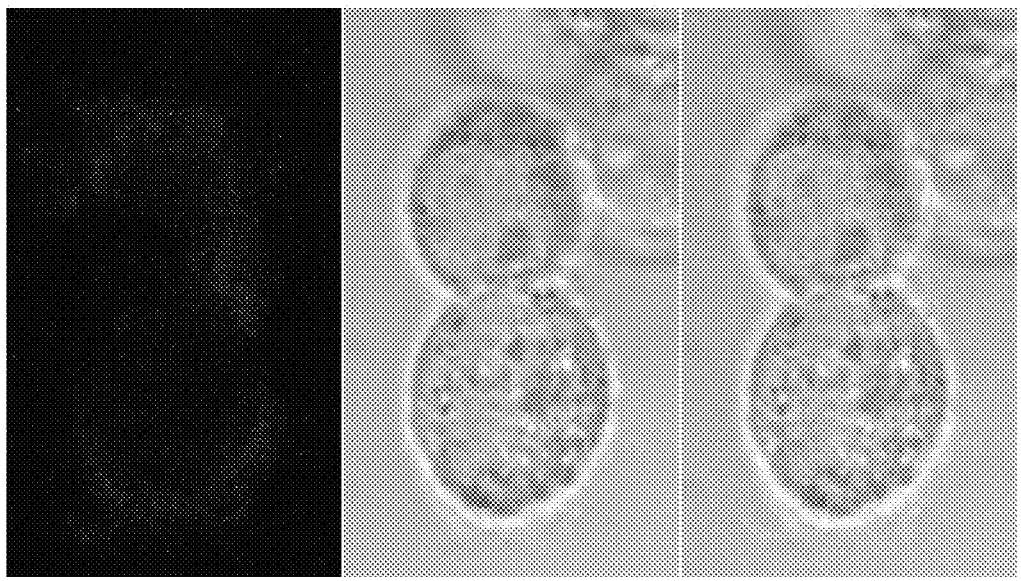
Figures 2D, 2E, 2F:
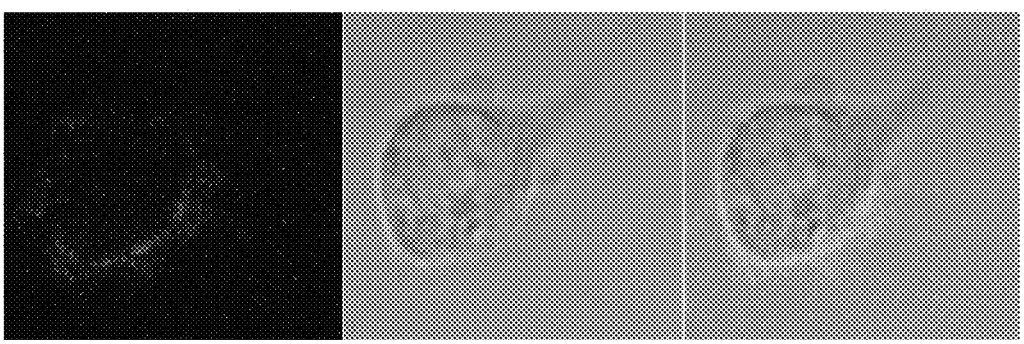

FIGS. 2A-F are Fluorescent confocal images of live human embryonic kidney (HEK293T) cells transiently transfected with plasmid DNA encoding the engineered FhuA$_{7/10}$-1. The rhodaminylated secondary antibody, which binds to the anti-His tag antibody can be seen in red. FIGS. 2A and 2D: Fluorescence; FIGS. 2B and 2E: Light bright field; FIGS. 2C and 2E: Merge of respective 2A and 2B and FIGS. 2D and 2E.

Figure 3:
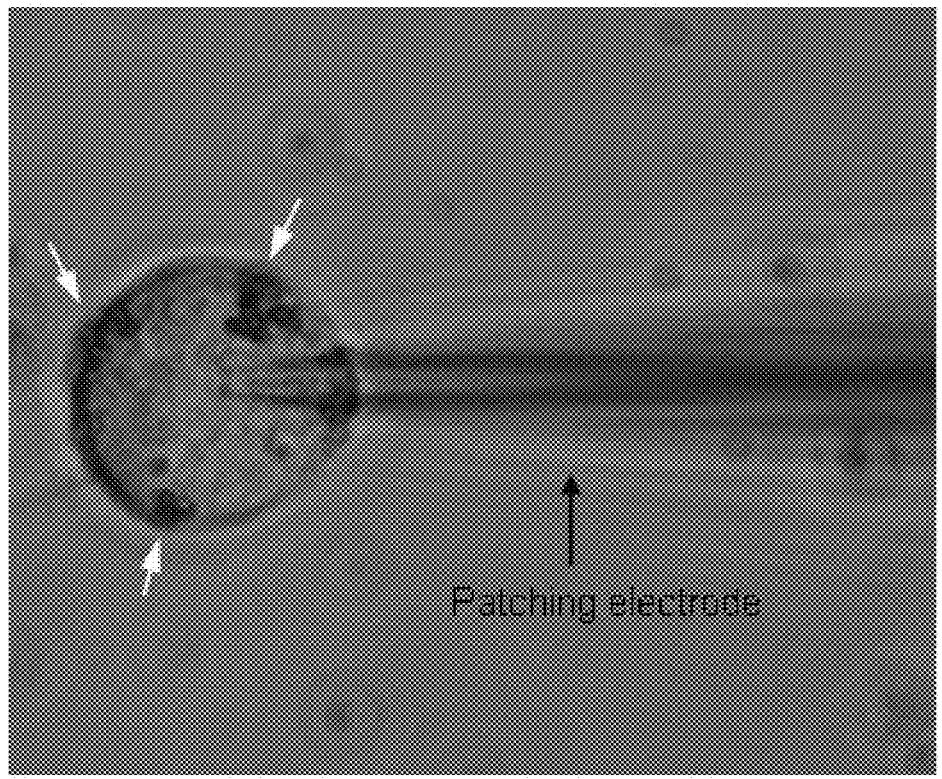

FIG. 3 is an image of a live HEK293T cell transiently transfected with DNA encoding the engineered FhuA$_{7/10}$-1. White arrows point to superparamagnetic polystyrene beads, which are coated with cobalt ions and therefore strongly bind the His tag. The His tag is inserted inside one of the extracellular loops of the engineered pore-forming polypeptide. The diameter of the beads is 1 μm and they have a dark red color. The patching electrode (~6 MΩ resistance) descends towards the cell and only its tip touches the cell membrane. Note that 48 hours after transfection the cells tend to lose their natural morphology and become round.

Figure 4:
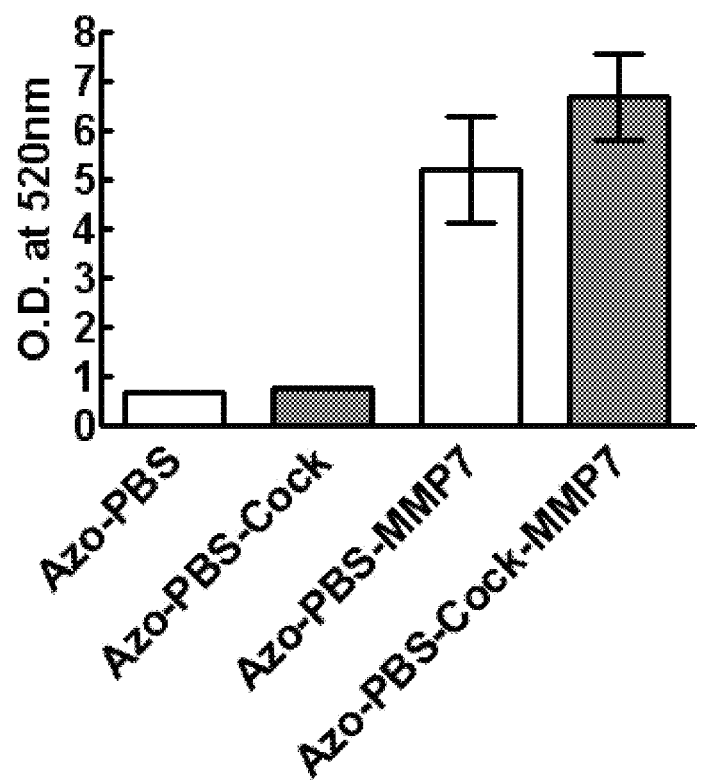

FIG. 4 is a bar graph illustrating that protease-inhibitor cocktail does not affect MMP-7 proteolytic activity. Azocoll, a general proteolytic substrate made from collagen with an embedded azo dye, yields a red color and absorbs at 520 nm upon its cleavage. Experiments were carried out in duplicates. Note that diluted amounts of sample were used for spectroscopic analysis so as not to oversaturate the spectrophotometer. Error bars represent the standard deviations of two independent experiments.

Figure 5A:
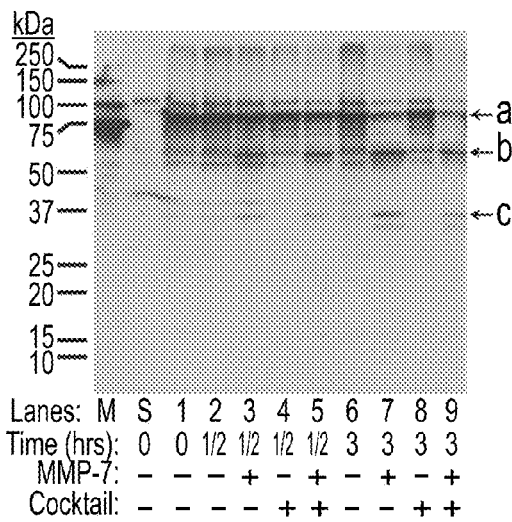
Figure 5B:
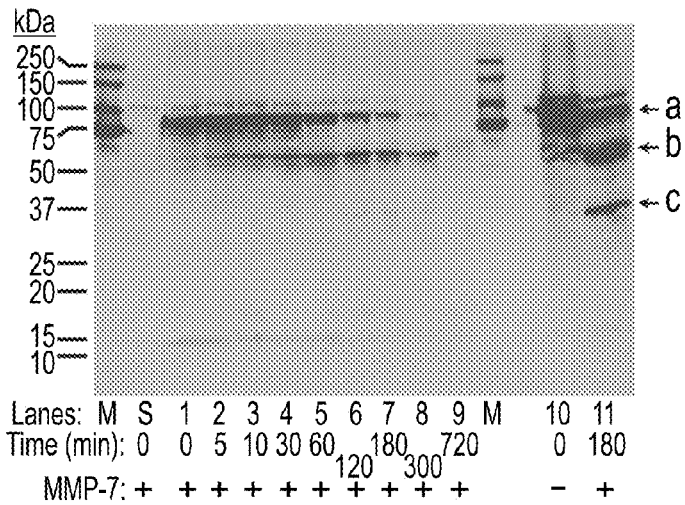
Figure 5C:
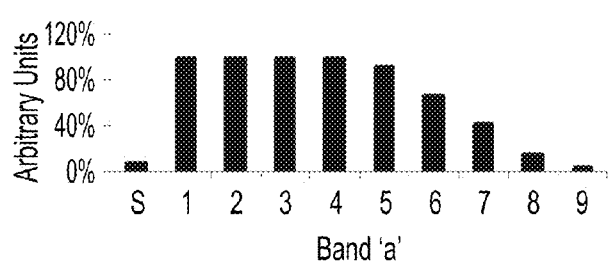
Figure 5D:
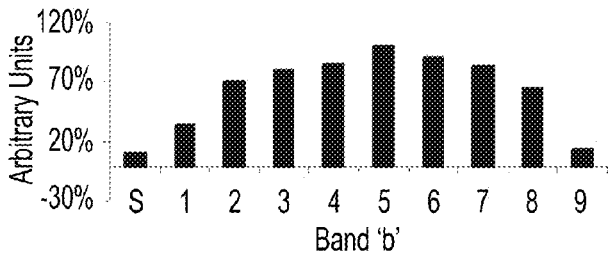
Figure 5E:
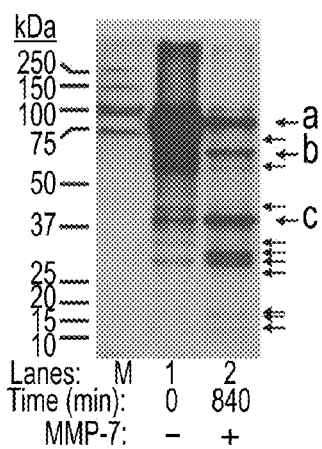

FIGS. 5A-E are graphs and images illustrating the cleavage of the engineered pore-forming polypeptide by MMP-7. FIG. 5A is a Western blot of membranes containing the pore-forming polypeptide (40 μg) incubated at 37° C. without or with MMP-7 (0.2 U/μl) for the indicated time. Cocktail is a protease inhibitor mixture that was tested for its ability to inhibit proteolysis inherent to membrane preparations without inhibiting MMP-7. FIG. 5B is a Western blot illustrating a Kinetics study of MMP-7 (0.2 U/μl) acting on the membranes (40 μg) that contain the engineered pore-forming polypeptide for periods of 0 to 720 min. Lanes 10 and 11 is an independent transfection where the engineered pore-forming polypeptide was overexpressed in an attempt to visualize additional cleavage products. FIGS. 5C-D are bar graphs illustrating the densitometry of FIG. 5B where arrows point to bands 'a' and 'b' respectively. FIG. 5E is an image of a PVDF blot that detects many cleavage products, 'a', 'b', and 'c' are those found on nitrocellulose blots (FIGS. 5A and 5B) while unlabeled arrows point to newly detected bands in lane 2.

M, molecular weight markers of which four markers bind anti-His antibodies. S, sham control of membranes (40 μg) prepared from CD8-transfected cells. On the right side of each gel, the letters a, b, and c point to the full-length engineered pore-forming polypeptide (~81 kDa) and its cleavage products ~57 kDa & ~37 kDa, respectively.

Figure 6:
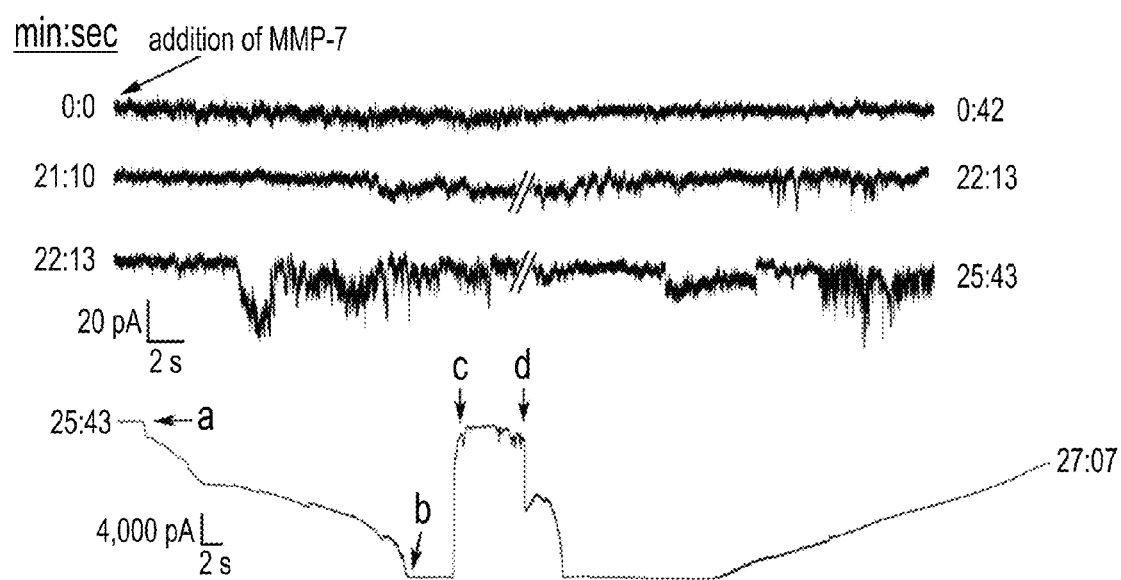

FIG. 6 are readouts of recordings illustrating ion permeation through the prototypic engineered pore-forming polypeptide. A cell identified to express the FhuA$_{7/10}$-1 pore-forming polypeptide (FIG. 3) was patched and human MMP-7 (0.4 U/μl) was then added to the recording bath (as indicated), at room temperature. In the first three recording lines, there are two sweeps per line; each sweep lasts 21 seconds. The first two sweeps are lined up consecutively, while the second and third sweeps are separated to indicate elapsed time. The fourth recording line corresponds to four consecutive sweeps. Recordings were performed at –60 mV.

Figure 7A:
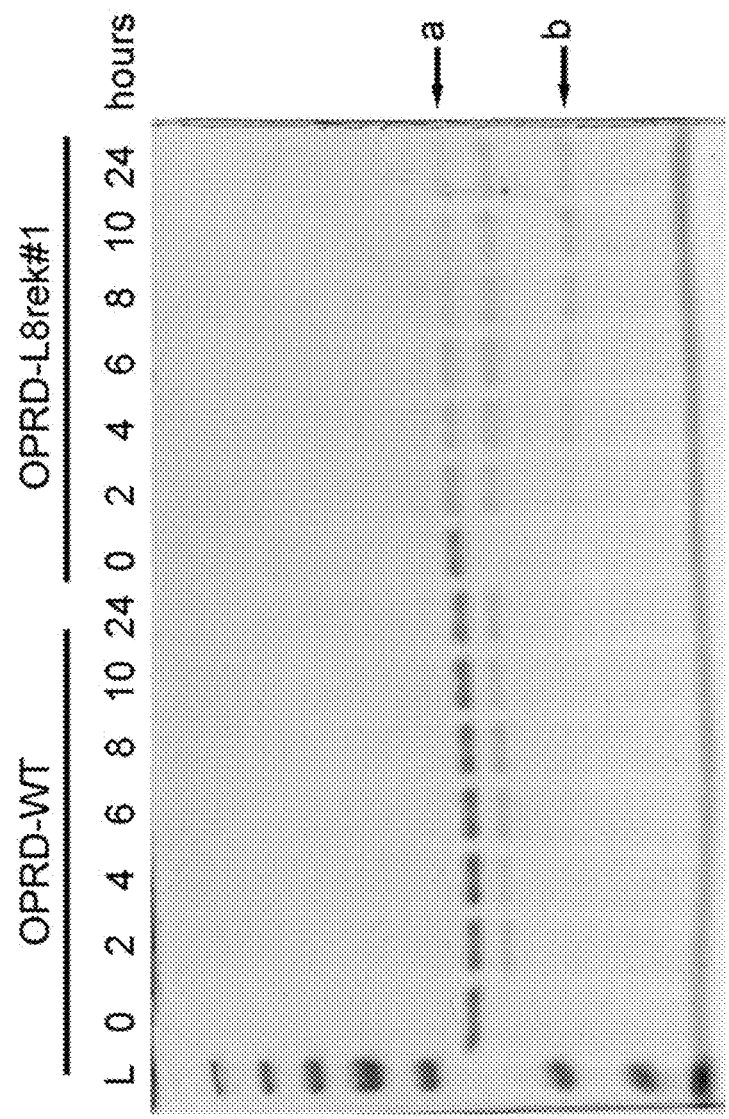
Figure 7B:
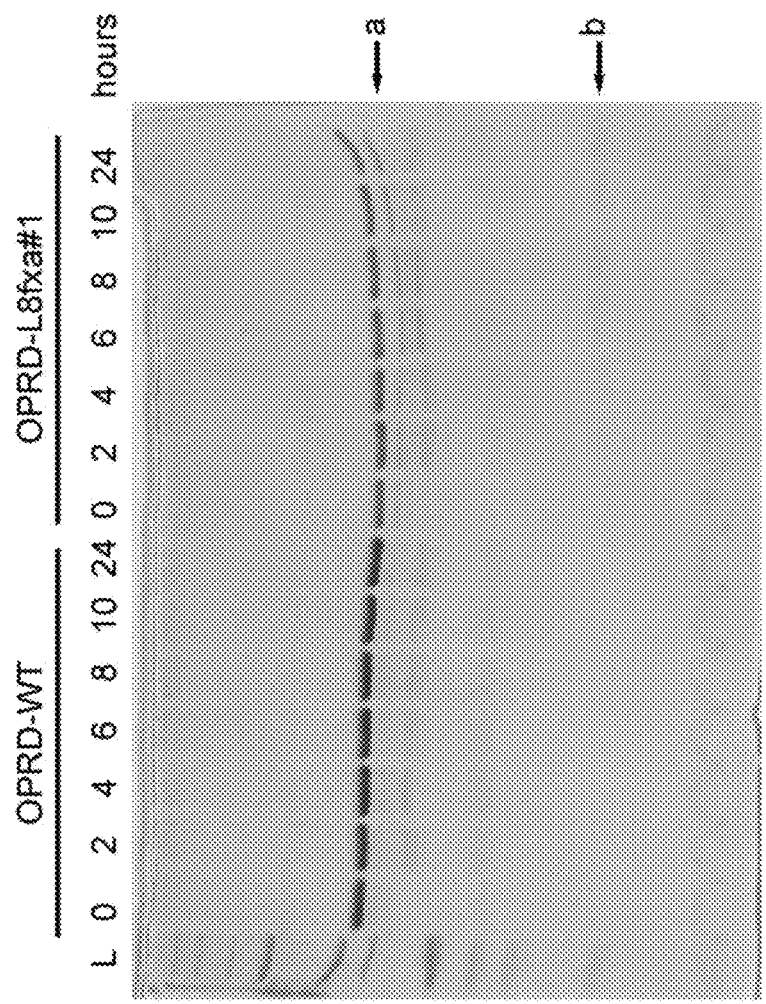
Figure 7C:
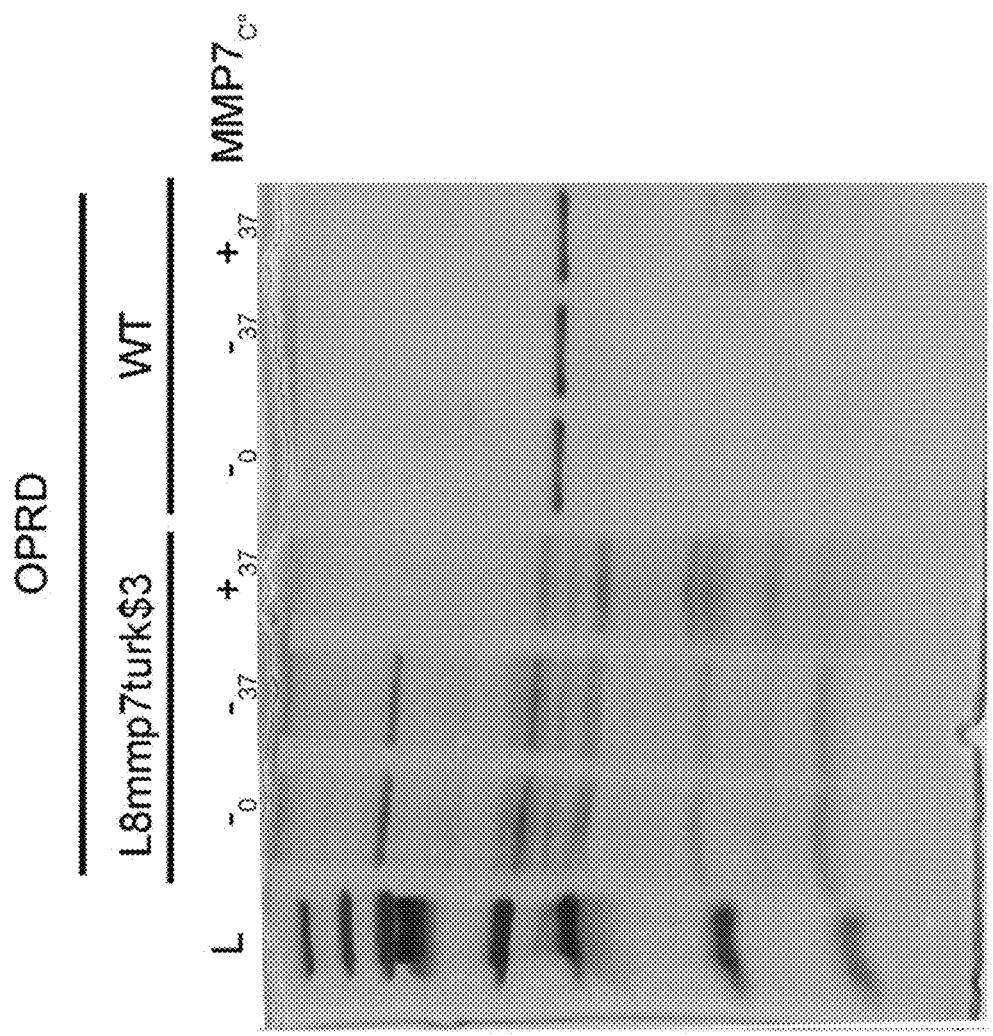

FIGS. 7A-C are images showing proteolysis of wild-type and mutant OprD incubated with the indicated proteolytic enzymes. FIG. 7A—Incubation of enterokinase with the wild type OprD yields a non specific band, that does not increase over time. However, incubating enterokinase with the mutant L8rek#1 (SEQ ID NO: 22798) shows specific cleavage since band "a" disappears and band "b" becomes more apparent over time. FIG. 7B—Incubation of Factor X enzyme with the wild type OPRD yields a few non specific bands. However, incubation of factor X with mutant L8fxa#1 (SEQ ID NO: 22788) shows specific cleavage, since bands "a" and "b" become more apparent with time. FIG. 7C—Incubation of MMP7 with wild type OprD yields a few non specific bands, compared with the control sample held at the same temperature for 24 hours but with out the MMP7. However, incubating mmp7 with the mutant L8mmp7turk#3 (SEQ ID NO: 22836) shows cleavage as the main protein band disappears.

Figure 8C:
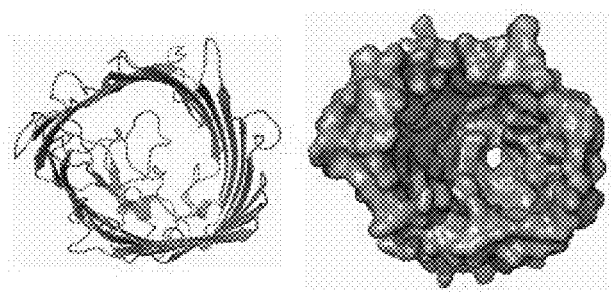
Figure 8B:
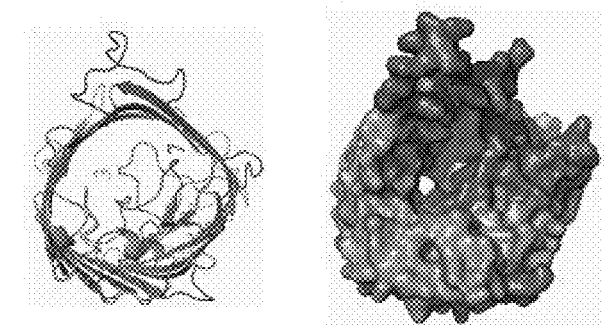
Figure 8A:
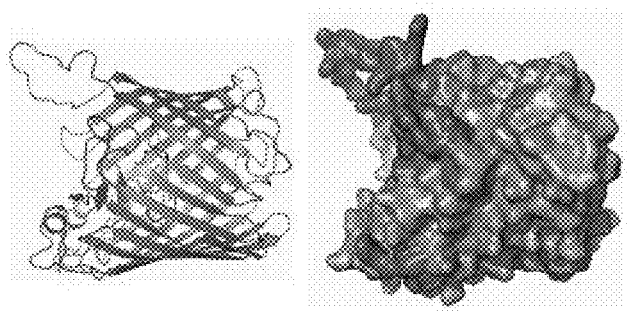

FIGS. 8A-C is a structural model for the full-length OprD. Upper panels: ribbon diagrams showing the β-barrel core in green, loops and helices which structure was solved by X-ray crystallography in salmon color, and loops which structure was determined by homology modeling in blue. Lower panels: solvent accessible surface of the structures shown in the upper panel with the same color code. FIG. 8A—Side view. FIG. 8B—Top view into the periplasmic space. Loops L3 and L7 are indicated in the upper panel. FIG. 8C—Bottom view, from the periplasmic space.

FIGS. 9A-B show that removal of a few loops opens up the pore of OprD. FIG. 9A shows the surface of OprD which pore-located loops have been removed. A Doxorubicin molecule (spheres) is centered in the middle of OprD. The loops that have been removed are L3, L7, L8 and L4. FIG. 9B is an alignment showing WT OprD and an OprD with amino acid sequences that were cut out (gaps, SEQ ID NO: 22984 and 22985) in silico.

DESCRIPTION OF SPECIFIC EMBODIMENTS OF THE INVENTION

The present invention, in some embodiments thereof, relates to pore-forming polypeptides that are naturally plugged and that are engineered to open by the action of proteases. The engineered pore-forming polypeptides may be incorporated at the surface of encapsulating particles such that they generate permeable pores (e.g. drug-permeable pores) in the particles only upon exposure to specific proteases. Opening of the pores releases the content of the encapsulating particle.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The delivery of therapeutic agents to solid tumors is a significant problem because of transport barriers that limit the delivery of drugs to the tumor site. A second problem in cancer therapy is that chemo- and radio-therapeutic agents are typically toxic to healthy cells as well as tumor cells, which leads to undesirable side effects during anticancer therapy. In an attempt to overcome these problems in cancer therapy, different types of drug delivery systems have been developed that employ macromolecules, vesicles, or particles as carriers for therapeutics. In general, these systems seek to maximize localization of the drug to the tumor while minimizing systemic toxicity. Although some of these approaches have shown promise in preclinical studies, there is significant room for improvement in the design of drug targeting systems for cancer therapy.

The present inventors have conceived of a novel drug delivery system that relies on a protease-sensitive pore-forming polypeptide for drug release from an encapsulating particle. The protease-sensitive pore-forming polypeptide comprises a modified pore protein that has been engineered such that the pore opens in the presence of a disease-associated protease.

As a prototype, the present inventors have introduced ten MMP-7 cleavage sites into loops and β strands of the pore-protein FhuA. The present inventors showed that the mutated FhuA beta barrel is expressed on the cell surface of HEK cells, and therefore it is inferred that the transmembrane topology of the genetically modified protein is similar to that of the wild-type (FIGS. 2A-F and FIG. 3). In addition, the present inventors showed that human MMP-7 was capable of cleaving the engineered FhuA in a membrane preparation where the engineered pore-forming polypeptide is integrated and folded in its natural environment, within the lipid bilayer (FIGS. 5A-B). Voltage-clamp experiments showed that prior to MMP-7 administration, the engineered FhuA remains tightly sealed, and does not allow the passage of ionic current (FIG. 6). OprD was used as a second prototype in which Loop 8 was shown accessible to enzymatic cleavage by a number of highly specific proteases (Faxtor X and enterokinase) as well as by the cancer associated human MMP-7 (FIGS. 7A-C). The proteins were successfully expressed in E. coli, substantiating their use as a drug delivery system.

The present inventors propose similar drug delivery systems for any disease which is associated with expression of a protease.

Thus, according to one aspect of the present invention there is provided an isolated pore-forming polypeptide comprising a naturally-occurring plugging module and a naturally-occurring pore domain, wherein at least one amino acid of the pore-forming polypeptide is mutated to generate a protease cleavage site. The protease cleavage site serves to at least partially remove the plugging module from the pore domain.

The phrase "pore-forming polypeptide" refers to a transmembrane polypeptide that naturally comprises i) a pore (i.e. channel) and ii) a plug (also referred to herein as a cork) which is capable of closing the pore. Accordingly, the pore-forming polypeptide of the present invention is of a size and shape which allows it to traverse the majority of a width of a membrane bilayer. According to one embodiment, the pore-forming polypeptide is capable of forming a pore spanning the entire length of a membrane bilayer.

According to one embodiment, the pore-forming polypeptide is a mutated (engineered) prokaryotic polypeptide.

The pore-forming domain of the polypeptide refers to the transmembrane domain of the polypeptide. According to one embodiment, the transmembrane domain comprises a β barrel structure. A detailed description of the β-barrel structure is disclosed in WO97/35022, incorporated herein by reference. According to another embodiment, the pore domain comprises an alpha helical structure.

Preferably, the pore-forming polypeptide forms a pore as a single unit or monomer.

The pore of the pore-forming polypeptide, at its minimum, must be wide enough to at least allow the passage of water when the plug is fully removed. According to one embodiment, the pore of the pore-forming polypeptide is at least 0.4 nm and more preferably at least about 1 nm when fully opened to allow water (~0.3 nm) to traverse the channel (even through cavities lined by hydrophobic amino acid side chains). According to another embodiment, the pore of the pore-forming polypeptide is between about 0.4 nm-10 nm and more preferably between about 1.4 nm-10 nm when fully open.

As mentioned, the pore-forming polypeptides of this aspect of the present invention also comprise a naturally occurring plugging module. The plugging module is such that it does not allow the flow of drugs or water via the pore, in both its naturally occurring state and modified state—i.e. it renders the pore non-leaky. The plug can be composed of, a single plugging domain (as in for example FhuA), or made up of several loops that are part of the protein (as in for example OprD). These loops can form a cap or plug on top of, or in the pore. The plugging module can be composed of a beta sheet, an alpha helix, or a loop structure (random coil) or any of these combinations.

Exemplary polypeptides which may be used to generate the pore-forming polypeptides of the present invention are those that belong to the family of Ton-B dependent receptors.

Examples of Ton-B dependent receptor polypeptides include, but are not limited to BtuB CirA, FatA, FcuT, FecA, FhuA FhuE, FepA, FptA, HemR, IrgA, IutA, PfeA, PupA and Tbp1.

Other exemplary polypeptides which may be used to generate the pore-forming polypeptides of the present invention are those that belong to the family of OprD outer membrane proteins.

Examples of OprD polypeptides include, but are not limited to OprE (GenBank Ref No: D12711); OpdT (GenBank Ref No: AF033849); and OprD (GenBank Ref No: X63152).

According to a specific embodiment the pore-forming polypeptide is OprD. A structural model of OprD is provided in FIGS. 8A-C. The present inventors have found that OprD is easily solubilized and therefore may be advantageously used along with the teachings of the present invention. The plugging domain is composed of a crown of loops at the top of the molecule which is readily accessible to enzymes for shearing. The crystal structure of OprD is available from http://wwwdotpdbdotorg/pdb/explore/explore.do?structureId=2ODJ, which is herein incorporated by reference in its entirety. Elecrophysiological studies have shown that the channel is non leaky and plugged in the wild type form. OprD was previously introduced into liposomes (Yoshihara J. Biol chem., 1989 v264: 6297-301, the teachings of which being incorporated by reference in their entirety).

Table 1A, below, lists the loop domains of OprD.

As used herein a "loop" is defined by a three dimensional structure not being a beta-strand, and an additional 3 amino acids upstream or downstream thereto.

According to a specific embodiment the mutation in the at least one amino acid is in a tier2 loop which is a corking loop. A tier2 loop is L3, L7 or a combination of same.

Mutations in Tier1 loops are also contemplated. According to a specific embodiment the mutation is in L5, preferably L6, more preferably L9, even more preferably L4 and most preferably L8.

According to a specific embodiment the mutation is in a combination of a Tier2 loop and a Tier1 loop.

According to a further specific embodiment, the mutation is located in L3, L7. L4 and L8 in accordance with the model provided in FIGS. 9A-B.

The present teachings also envisage mutations in the bottom loops, which face the periplasmic space, see FIG. 89A. Such mutations may govern the orientation in the encapsulating particle. Such mutations are provided in SEQ ID NOs: 22804, 22842, 22882 and 22954.

TABLE 1A

| | |
|---|---|
| L1 | nrdGKSGSGDRVdwt/22988 |
| L2 | kldGTSDKTGTGNLPVMNDGKPRDDysr/22989 |
| L3 | lkwGEMQPTAPVFAAGGSRLFPQTATgfq/22990 |
| L4 | ghfTEGKEPTTVKSRGELYATYAGETAKSadf/22991 |
| L5 | aelEDIyrq/22992 |
| L6 | rtnDEGKAKAGDIsnt/22993 |
| L7 | kvhGDQPFDYIGFGRNGSGAGGDSIFLANSVQYSDFNGPgek/22994 |
| L8 | ngkDIDGTKMSDNNVGYKNYGYGEDGKhhe/22995 |
| L9 | hraNADQGEGDqne/22996 |
| BL1 | FVSDQAEAKGFIEDSsld/22997 |
| BL2 | tyeSGFTQGTVgfg/22998 |
| BL3 | vriSKtml/22999 |

TABLE 1A-continued

| | |
|---|---|
| BL4 | lqsSEFEGldl/23000 |
| BL5 | yaiTDNlsa/23001 |
| BL6 | iplASDqsl/23002 |
| BL7 | ytlDAhtf/23003 |
| BL8 | dlnLASYGVPGLltf/23004 |
| BL9 | kyvVQSGPAKDLsfr/22982 |

Abbreviations - top crowning loops (L) bottom loops (BL). The lower case letters are part of the beta-strands directly before and after the loops, but for the context of this invention, they are to be considered part of the loop structures. The sequences can be aligned to Wild Type OprD P32722 (PORD_PSEAE).

TABLE 1B

| Structural | | Example of Mutant | | | |
|---|---|---|---|---|---|
| location | Loop | MMP7 | MMP2 | MMP9 | reK |
| Crowning | L1 | L1mmp7turk | L1mmp2turk | L1mmp-9 | L1rek |
| Tier 1 | L8 | L8mmp7turk#1 | L8mmp2turk#2 | L8-mmp9#1 | L8rek#1 |
| Crowning | L3 | L3mmp7turk#1 | L3mmp2turk#2 | L3-mmp9#3 | L3rek$3 |
| Tier 2 | L7 | L7mmp7turk#1b | L7mmp2turk#1 | L7-mmp9#2b | L7rek#1b |
| Bottom | BL | BL7mmp7turk | BL7mmp2turk | BL7-mmp9 | BL7rek |

Specific examples of OprD sequences which can be used in accordance with the teachings of the present invention are set forth in SEQ ID NOs: 22778, 22780, 22782, 22784, 22786, 22788, 22790, 22792, 22794, 22796, 22798, 22800, 22802, 22804, 22806, 22808, 22810, 22812, 22814, 22816, 22820, 22822, 22824, 22826, 22828, 22830, 22832, 22834, 22836, 22838, 22840, 22842, 22844, 22846, 22848, 22850, 22852, 22854, 22858, 22860, 22862, 22864, 22866, 22868, 22870, 22872, 22874, 22876, 22878, 22880, 22882, 22884, 22886, 22888, 22892, 22894, 22898, 22900, 22902, 22904, 22906, 22908, 22910, 22912, 22914, 22916, 22918, 22920, 22922, 22924, 22926, 22928, 22930, 22932, 22934, 22936, 22938, 22940, 22942, 22944, 22946, 22948, 22950, 22952, 22954, 22956, 22958, 22960, 22962 and 22986).

Of note, the above sequences are provided as mere examples; however it will be appreciated by the skilled artisan that there is flexibility in the position of the mutation (e.g., 2, 3, 4 or 5 amino acids N-terminally or C-terminally of the proposed location, indicated by arrows above) and the nature of the mutated sequence. Expression and activity assays for qualifying the mutated sequences are provided hereinbelow and in the Examples section which follows.

Other exemplary polypeptides which may be used to generate the pore-forming polypeptides of the present invention are those that belong to the following families of polypeptides, as described in: http://pfamdotsangerdotacdotuk/clan/MBB:

IPR000531 TonB-dependent receptor, beta-barrel;
IPR001702 Porin, Gram-negative type;
IPR005318 Outer membrane porin OprD, bacterial;
InterPro IPR018013 Nucleoside-specific channel-forming protein, Tsx-like;
IPR000036 Peptidase A26, omptin;
IPR000498 Outer membrane protein, OmpA-like, transmembrane region;
IPR000758 Virulence-related outer membrane protein;
IPR002718 Outer membrane protein, *Helicobacter*;
IPR003055 Nucleoside-specific channel-forming protein, Tsx;
IPR003394 Porin, opacity type;
IPR003684 Porin, alpha proteobacteria type;
IPR005017 Membrane protein involved in aromatic hydrocarbon degradation;
IPR005546 Autotransporter beta-domain;
IPR005618 Outer membrane protein, OmpW;
IPR007049 Carbohydrate-selective porin OprB;
IPR008722 OmpF;
IPR009331 Oligogalacturonate-specific porin;
IPR009746 Antimicrobial peptide resistance and lipid A acylation PagP;
IPR010870 Phosphate-selective porin OP;
IPR011250 Outer Membrane Protein Beta-Barrel;
Outer membrane protein G (OmpG); and
PagL (PF09411)

According to one embodiment, the pore-forming polypeptide of the present invention comprises a sequence as set forth in SEQ ID NOs: 24-22778, 22780, 22782, 22784, 22786, 22788, 22790, 22792, 22794, 22796, 22798, 22800, 22802, 22804, 22806, 22808, 22810, 22812, 22814, 22816, 22820, 22822, 22824, 22826, 22828, 22830, 22832, 22834, 22836, 22838, 22840, 22842, 22844, 22846, 22848, 22850, 22852, 22854, 22858, 22860, 22862, 22864, 22866, 22868, 22870, 22872, 22874, 22876, 22878, 22880, 22882, 22884, 22886, 22888, 22892, 22894, 22898, 22900, 22902, 22904, 22906, 22908, 22910, 22912, 22914, 22916, 22918, 22920, 22922, 22924, 22926, 22928, 22930, 22932, 22934, 22936, 22938, 22940, 22942, 22944, 22946, 22948, 22950, 22952, 22954, 22956, 22958, 22960, 22962, 22986, 22964-22981.

Other exemplary pore-forming polypeptides which comprise a naturally occurring plug may be selected from the PFAM database, which comprises a library of outer membrane beta-barrel protein superfamily (http://pfamdotsangerdotacdotuk/clan?id=MBB and www.ebi.ac.uk/interpro/). Other databases which may be used for selecting the polypeptide include the BOMB database (http://servicesdotcbudotuibdotno/tools/bomp); the University of Leeds TMBC-fa database; and the K-12-tmbeta-genome db http://tmbetagenomedotcbrcdotjp/annotation/.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids, as well as glycosylated amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |

TABLE 3-continued

| Non-conventional amino acid | Code | Non-conventional amino acid | Code |
|---|---|---|---|
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-αthylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-αethylhistidine | Mhis | L-α-methylhomophenylalanine | Mhphe |
| L-αthylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-αethylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenylethylamino)cyclopropane | Nmbc | | |

As mentioned, the polypeptides of this aspect of the present invention are genetically modified to incorporate a protease cleavage site.

As used herein, the phrase "modified polypeptide" refers to a polypeptide comprising an amino acid modification (i.e. mutation) as compared to the wild-type polypeptide. Any modification to the sequence is envisaged according to this aspect of the present invention so long as the pore of the polypeptide remains tightly sealed in the absence of pathological concentrations of the disease-associated protease and is capable of opening in the presence of pathologically-elevated concentrations of the disease-associated protease.

According to one embodiment, the protease of the protease cleavage site is associated with a disease.

In one embodiment of the invention, the protease is one that is associated with cancer invasion and metastasis in general. In another embodiment, the protease is one which is up-regulated and/or secreted by cancer cells. In still another embodiment, the protease is activated by receptors expressed by cancer cells.

Examples of such proteases include the matrix metalloproteinase (MMP) family, the elastase, and the plasminogen activator family tPA uPA, fibroblast activation protein, cathepsins, kallikreins, plasmin and thrombin.

Based on structural features (including the amino acid sequences, domain organizations), 26 different types of MMPs have been recognized in human tissues, which fall into five major classes: (i) collagenases, (ii) gelatinases, (iii) stromelysins and stromelysin like MMPs, (iv) matrilysins, (v) membrane type MMPs, and (vi) other MMPs (viz., MMP-20, MMP-23, and MMP-28) (M. Whittaker et al., Chem. Rev., 1999, 99, 2735-2776; G. Murphy et al., Methods Enzymol., 1995, 248, 470-484; R. Kiyama et al., J. Med. Chem., 1999, 42, 1723-1738). Although many of these MMPs have been implicated in different types of human diseases, gelatinase-A (MMP-2) and gelatinase-B (MMP-9) have been widely recognized to be involved in the progression and metastasis in most of the human tumors. Gelatinase-A and -B have been found to be overexpressed in breast tumors, (M. Polette et al., Virchows Arch Int. J. Pathol., 1994, 424, 641-645; K. Dalberg et al., World J. Surg., 2000, 24, 334-340; R. Hanemaaijer et al., Int J Cancer, 2000, 86, 204-207) colorectal tumors, (S. Papadopoulou et al., Tumour Biol., 2001, 22, 383-9; J P Segain et al., J. Cancer Res., 1996, 56, 5506-12) lung tumors, (M. Tokuraku et al., Int J. Cancer., 1995, 64, 355-359; H. Nagawa et al., S. Jap. J. Cancer Res., 1994, 85, 934-938) prostate tumors (G. Sehgal et al., Am. J. Pathol., 1998, 152, 591-596), pancreatic tumors (T. Koshiba et al., Surg Today., 1997, 27, 302-304; T M Gress et al., Int J. Cancer., 1995, 62, 407-413), and ovarian tumors (T N Young et al., Gynecol Oncol., 1996, 62, 89-99). In fact, the initial discovery of the involvement of MMPs in melanoma cancer and metastasis were ascribed to be due to the overexpression of gelatinase-A and -B (V. Kahari et al., Exp. Dermatol., 1997, 6, 199-213; U. Saarialho-K, Arch. Dermatol., 1998, 294, S47-S54; H. Nagase et al., J. Biol. Chem., 1999, 274, 21491-21494; E. Kerkela et al., Exp. Dermatol., 2003, 12, 109-125; A. R. Nelson et al., J. Clin. Oncol., 2000, 18, 1135-1149; L. A. Liotta et al., Nature, 1980, 284, 67-68). Additionally, MMP-14 (MT1-MMP) has been suggested to be overexpressed in every form of cancer, if not the cause of many malignant transformations (Golubkov et al. 2005 Membrane type-1 matrix metalloproteinase (MT1-MMP) exhibits an important intracellular cleavage function and causes chromosome instability, Biol Chem 280:25079-25086.

Examples of proteases of the plasminogen activator family include uPA (urokinase-type plasminogen activator) and tPA (tissue-type plasminogen activator).

It will be appreciated that the present invention contemplates protease cleavage site which are associated with diseases other than cancer. For example, gelatinase-A and -B have been found to be involved in gouty arthritis (M S Hsieh et al., J Cell Biochem., 2003, 89, 791-799), inflammatory bowel disease (ulcerative colitis) (E. Pirila et al., Dig Dis Sci., 2003, 48, 93-98), abdominal aortic aneurysms (R. Pyo et al., J Clin Invest., 2000, 105, 1641-1649), quiescent Crohn's Disease (A E Kossakowska et al., Ann N Y Acad. Sci., 1999, 878, 578-580), glaucoma (C. Kee et al., J. Glaucoma., 1999 8, 51-55), and sunlight induced premature skin aging (G J Fisher et al., Curr Opin Rheumatol., 2002, 14, 723-726).

In addition, gelatinase-B has been found to play a role in arthritis or in neurodegenerative diseases such as multiple sclerosis (Firestein, Curr. Opin. Rheumatol. 4:348-354 (1992); Gijbels et al., J. Neuroimmunol. 41:29-34 (1992)). For example, high levels of gelatinase-B have been detected in serum and synovial fluid of patients with inflammatory arthritis such as rheumatoid arthritis compared to healthy patients or patients with osteoarthritis (Ahrens et al., Arthritis & Rheumatism 39:1576-87 (1996); Gruber et al., Clin. Immunol. & Immunopathol., 78:161-171 (1996)). In addition, a correlation has been reported between the arthritic activity score of a joint and the amount of gelatinase-B in the aspirated synovial fluid (Koolwijk et al. J. Reumatology, 22:385-393 (1995)).

Expression of gelatinase-B is also detected in diseases of the nervous system. For example, prominent expression of gelatinase-B has been found in reactive astrocytes and macrophages in demyelinating lesions compared to normal brain tissue (Cuzner et al., J. Neuropathol. Exp. Neurol, 55:1194-1204 (1996)). MMP-9 is elevated in encephelomyelitis (Gijbels, et al. J. Neuro. Res. 36:432-440 (1993); Proost, et al., Biochem, Biophys, Res. Comm. 192:1175-1181 (1993)), in the cerebrospinal fluid of patients with multiple sclerosis (Leppert, et al., Brain 121:2327-2334 (1998); Rosenberg et al., Brain Res., 703:151-155 (1995)), and in patients with AIDS-related dementia (Conant, et al., Annals of Neurology 46: 391-398 (1999)). Furthermore, in patients with amyotrophic lateral sclerosis, gelatinase-B expression is found in the pyramidal neurons of the motor cortex and in the motor neurons of the spinal cord (Lim et al., J. Neurochem., 67:251-259 (1996)).

Gelatinase-B has also been associated with a variety of other inflammatory diseases. For example, a high level of MMP-9 activity is found in the vessel wall of aortic aneurysms (Freestone, et al. Arteriosclerosis, Thrombosis & Vascular Biology, 15:1145-1151 (1995); Newman et al., Connective Tissue Research, 30:265-276, (1994); Sakalihasan et al., J. Vascular Surgery, 24:127-33 (1996)). In addition, patients with giant cell arteritis have increased levels of MMP-9, and MMP-9 mRNA is found in smooth muscle cells and fibroblasts in the regions of fragmented elastic tissue in the lamina media of inflamed vessels (Sorbi, et al., Arthritis & Rheumatism, 35:1747-1753 (1996)). Increased levels of gelatinase-B are also found in sputum of patients with cystic fibrosis and in bronchoalveolar lavage fluids of those with bronchiectasis (Delacourt et al., Amer. J. Respiratory & Critical Care Med., 152:765-764 (1995); Sepper et al, Chest, 106:1129-1133 (1994)). High levels of gelatinase-B have also been found in blister fluids from the skin lesions of bullous pemphigoid patients (Stahle-Backdahl et al., J. Clinical Invest., 93:2022-2030 (1994)).

Gelatinase-B expression has also been implicated in the pathogenesis of several other diseases. For example, gelatinase-B has been implicated in polycystic kidney disease (Murray et al., Conn. Tissue Res., 33:249-256 (1996)), membranous nephropathy (McMillin et al., J. Clin. Invest., 97:1094-1101 (1996)), and Alzheimer's disease (Lim et al., J. Neurochem., 68:1606-1611 (1997)).

Non-limiting examples of selected cleavage sites recognized by some of these proteases are shown in Table 4 and further in the Examples section which follows.

Cleavage sites recognized by other proteases listed above are known in the art.

TABLE 4

| Protease | Forward cleavage sequence (*/* indictes site of cleavage) | SEQ ID NO: |
|---|---|---|
| Caspase 1 | YVAI/X | 17 |
| tPA | FGR/X | 18 |
| MMP14 | GGPLG/LYAGG | 19 |
| HK2 | GKAFRR/X | 20 |
| Thrombin | LVPR/GS | 21 |
| uPA | SGR/SAQ | 22 |

The cleavage site motif for a protease involves residues both N- and C-terminal to the scissile bond (the unprimed and primed sides, respectively, with the cleavage site for a protease defined as . . . P3-P2-P1-P1'-P2'-P3' . . . , and cleavage occurs between the P1 and P1' residues In general for creating an MMP cleavage sites the following criteria should be observed:

1. MMPs generally require hydrophobic amino acids at P1'☐ and prefer either hydrophobic or basic amino acids at P2'.

2. Whereas MMP-1, MMP-2, and MMP-9 prefer small residues (alanine, glycine, or serine) at P3', MMP-3, MMP-7, and MT1-MMP select for methionine at that position.

3. Although all MMP enzymes select aliphatic residues most strongly at P1', MMP-2, MMP-3, MMP-9, and MT1-MMP also had reasonable selections for phenylalanine and tyrosine at that position.

4. The major specificity site N-terminal to the scissile bond for all MMPs tested was at P3, where proline is preferred most strongly, although for most of the enzymes valine and isoleucine appear to be reasonable substitutions 5. The main selectivities for MMP-7 on the unprimed side in addition to proline at P3 are for hydrophobic residues (leucine, methionine, and tyrosine) at P2, and for serine, alanine, or glutamic acid at P1.

Table 5 herein below teaches preferred amino acids to generate MMP cleavage sites.

TABLE 5

| Common | | Cleavage Position | | | | | | | |
|---|---|---|---|---|---|---|---|---|---|
| Enzyme | Name | P5 | P4 | P3 | P2 | P1 | P1' | P2' | P3' |
| MMP-7 | Matrilysin | P | V | P | L | S | L | V | M |
|  |  | I | I | V | M | E | I | T | Y |
|  |  |  | R | I | Y | N | M | I | Q |
|  |  |  |  |  | A |  | M |  |  |
|  |  |  |  |  |  |  | K |  |  |
|  |  |  |  |  |  |  | R |  |  |
| MMP-1 | Collagenase-1 | V | V | P | M | S | M | M | A |
|  |  | I |  |  | Y | N | I | I | G |
|  |  |  |  |  | L | A | L | K | S |
|  |  |  |  |  | E |  | R |  |  |
| MMP-2 | Gelatinase A | D | I | P | V | S | L | R | S |
|  |  | L | V | V | A | G | M | Y | A |
|  |  | F |  | I |  | A | I | K | G |
|  |  | N |  |  |  | E | Y | M |  |
|  |  | I |  |  |  |  | F | I |  |
|  |  |  |  |  |  |  |  | V |  |
| MMP-9 | Gelatinase B | V | V | P | L | S | L | R | S |
|  |  |  |  | V | Y |  | M | T | A |
|  |  |  |  |  |  |  | I | Y | G |
|  |  |  |  |  |  |  | Y | V |  |
|  |  |  |  |  |  |  | F | I |  |
| MMP-3 | Stromelysin-1 | N | K | R | F | S | M | M | M |
|  |  | I | V | V | Y | E | I | K | A |
|  |  |  |  | I | L |  | L | I |  |
|  |  |  |  | R | M |  | Y | R |  |
|  |  |  |  |  | A |  | F |  |  |
| MT1-MMP | MMP-14 | F | I | P | X | S | L | R | M |
|  |  | L | K | V |  | A | I | K | A |
|  |  | D | V |  |  |  | M | Y |  |
|  |  | I | D |  |  |  | Y |  |  |
|  |  | V |  |  |  |  | F |  |  |

Further information for selecting cleavage sites for MMP enzymes may be found in Turk et al., Nature biotechnology, Volume 19, July 2001, incorporated herein by reference.

Additional MMPs and their recognition sequences are known in the literature, see for example, Netzelarnett S, Fields G, Birkedalhansen H, Vanwart H E. 1991. Sequence specificities of human fibroblast and neutrophil collagenases. J Biol Chem 266:6747-6755; Nagase H, Fields G B. 1996. Human matrix metalloproteinase specificity studies using collagen sequence-based synthetic peptides. Biopolymers 40:399-416; Deng S J, Bickett D M, Mitchell J L, Lambert M H, Blackburn R K, Carter H L, Neugebauer J, Pahel G, Weiner M P, Moss M L 2000. Substrate specificity of human collagenase 3 assessed using a phage-displayed peptide library. J Biol Chem 275:31422-31427; each of which is hereby incorporated by reference in its entirety.

Generally with reference to the polypeptides described herein but also with a specific reference to OprD, cleavage sites (e.g., MMP cleavage sites) are introduced into the plugging domain (crown loops at the top of the protein—tier one, and corking loops deeper within the protein—tier two, also cleavage sites are introduced to the bottom of the protein, see Table 1 above, and further examples above).

Since MMPs are known for their substrate sequence flexibility, modifications are also contemplated.

A specific generic sequence which is cleaved by MMP-7 is provided in SEQ ID NO: 22856 and Protein IVVLSLVM (SEQ ID NO: 23005), DNA ATTGTTGTTTTATCTTTAGT-TATG, SEQ ID NO: 23006 and SEQ ID NO: 22857). See e.g., Vargo-Gogola Biochemistry and Biophysics 408 (2002) 155-161, which is hereby incorporated by reference in its entirety. Likewise:

MMP2:

Protein: DIVVSLRS (SEQ ID NO: 22892)

DNA: GATATTGTTGTTTCTTTACGTTCT (SEQ ID NO: 22893)

```
                             -continued
MMP9
                                          (SEQ ID NO: 22928)
Protein: VVPLSLRS (SEQ ID NO: 22929)
DNA: GTTGTTCCTTTAAGTTTAAGATCT
```

OprD sequences which are implanted with these cleavage sequences are provided in SEQ ID NOs. 22888-22891, 22894-22927, 22930-22963 and 22986-22987.

Examples of modifications (e.g. mutations) contemplated by the present inventors include deletions, insertions and/or substitutions. Substitutions at one particular site on the polypeptide are typically in the range of about 1 to 20 amino acids, and more typically in the range of about 1 to 10 amino acids signifying the proteolysis cleavage site.

It will be appreciated that more than one cleavage site may be generated. According to one embodiment up to ten cleavage sites are generated. According to another embodiment up to fifteen cleavage sites are generated. The number of modifications made is typically restricted to a number that does not hinder the expression and folding of the polypeptide.

It will be further appreciated that the modifications to the polypeptide of the present invention may act to generate a protease cleavage site or alternatively to expose a protease cleavage site that naturally exists. According to one embodiment the polypeptide is modified at site x' to generate the protease cleavage site and further modified at site y' to allow better access of the protease to site x'. Alternatively or additionally, cleavage at site y' may help to weaken the overall 3-D structure of the protein of choice.

As mentioned, the pore-forming polypeptide may be modified such that the plugging module is completely removed from the pore domain thereby allowing passage of any molecule which has dimensions less than or equal to the width of the pore. Alternatively, the pore-forming polypeptide may be modified such that the plugging module is only partially removed from the pore domain, such that water is able to travel through the pore. Accordingly, the number of modifications will also depend on the extent of removal of the plugging module from the pore domain required, whereby complete removal of the plugging module may require more modifications than only partial removal of the plugging module from the pore domain.

The sites of modification are typically selected according to the suggested 3D structure of the pore-forming polypeptide. Thus, for example, modifications at site y' typically occur on outer loops of the polypeptide. Thus for example the modification may be on a loop that faces the extracellular milieu, periplasmic space, cytoplasmic space or spaces surrounded by inner membranes.

Modifications which serve to open the pore of the pore-forming polypeptide are typically made at the plugging-module itself (x').

Preferably, the modified polypeptide of this aspect of the present invention comprises at least one protease cleavage site on an outer loop of the polypeptide. Alternatively, or additionally, the protease cleavage site may be comprised on the loop connecting the pore domain with the plug domain.

According to one embodiment, conservative amino acid substitutions are made such that folding and subsequent expression of the polypeptide is not impaired. The conservative amino acid substitution may be effected at a predicted, non-essential amino acid residue.

A “conservative amino acid substitution” is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

According to one embodiment, the bond networks of the native and substituting amino acids are considered when selecting a particular modification. For example, native amino acid side-chains which face into the protein may interact via H-bonds with other amino acids, therefore, the mutating amino acid should attempt to keep this same interaction. To this end, the volume of the amino acid’s side chain, its charge, and overall chemical structure (aromatic side-chains in particular) should be kept similar. Hydrophobicity of amino acid side chains located at the perimeter of the pore domain also play an important role in determining the pore-forming polypeptide placement in a lipid bi-layer; therefore, polar and non-polar side chains should be kept constant during mutagenesis.

In some instances, protease cleavage sites have a requirement for a particular amino acid. Thus, as described herein above, an MMP-7 cleavage site typically comprises a proline at position P3. Accordingly, for generation of MMP-7 cleavage sites, loops that comprise native prolines may be preferred sites for mutation.

An exemplary amino acid sequence of a Fhu-A polypeptide that has been modified such that its pore domain is capable of opening in the presence of MMP-7 is provided in SEQ ID NOs: 5 or 7.

It will be appreciated that the pore-forming polypeptides of the present invention can also include sequences engineered to optimize stability, production, purification, yield or activity thereof. Such sequences may also aid in cell surface identification. These sequences can further comprise a cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

Typically, the polypeptide is engineered such that the affinity tag is placed on one of its solvent accessible extracellular loops.

Thus, for example the pore-forming polypeptide of the present invention may comprise a histidine affinity tag (or other tags such as FLAG or hemagglutinin).

An exemplary amino acid sequence of a Fhu-A polypeptide that has been modified such that its pore domain is capable of opening in the presence of MMP-7 and further comprises a histidine tag is provided in SEQ ID NO: 5.

The isolated polypeptides of present invention can be biochemically synthesized such as by using standard solid phase techniques. These methods include exclusive solid phase synthesis, partial solid phase synthesis methods, fragment condensation, classical solution synthesis. These methods are preferably used when it cannot be produced by recombinant techniques (i.e., not encoded by a nucleic acid sequence) and therefore involves different chemistry or when short peptides are synthesized.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques are preferably used to generate the isolated polypeptides of the present invention since these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce the isolated polypeptides of the present invention using recombinant technology, an isolated polynucleotide comprising a nucleic acid sequence encoding such a polypeptide may be used. Exemplary nucleic acid sequences are set forth in SEQ ID NOs: 6 and 8.

The term "nucleic acid sequence" refers to a deoxyribonucleic acid sequence composed of naturally-occurring bases, sugars and covalent internucleoside linkages (e.g., backbone) as well as oligonucleotides having non-naturally-occurring portions which function similarly to respective naturally-occurring portions. Such modifications are enabled by the present invention provided that recombinant expression is still allowed.

A nucleic acid sequence of the pore-forming polypeptides of this aspect of the present invention can be a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

In order to generate the pore-forming polypeptides of the present invention using recombinant techniques, the polynucleotides encoding same are ligated into nucleic acid expression vectors, such that the polynucleotide sequence is under the transcriptional control of a cis-regulatory sequence (e.g., promoter sequence).

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Constitutive promoters suitable for use with this embodiment of the present invention include sequences which are functional (i.e., capable of directing transcription) under most environmental conditions and most types of cells such as the cytomegalovirus (CMV) and Rous sarcoma virus (RSV).

Inducible promoters suitable for use with this embodiment of the present invention include for example the tetracycline-inducible promoter (Srour, M. A., et al., 2003. Thromb. Haemost. 90: 398-405) or IPTG.

The expression vector according to this embodiment of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression vector in order to increase the translation efficiency of a polypeptide expressed from the expression vector of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Expression vectors containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of the present invention.

An exemplary prokaryotic host-expression system contemplated by the present invention is *E. coli* strain BL 21 (DE3) omp8 (which lacks all major porins—OmpF, OmpC, PhoE, LamB, OmpA).

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Examples of mammalian expression vectors include, but are not limited to, pcDNA3, pcDNA3.1 (+/−), pGL3, pZeoSV2 (+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

It will be appreciated that the coding sequence may be modified according to the expression system used. For instance, to optimize expression, a native signal peptide may be used or replaced with a heterologous signal peptide. An exemplary heterologous FadL signal peptide is as set forth in SEQ ID NO: 22983.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Outer membrane fractions may initially be obtained using methods known in the art—see for example Erick-Helmerich and Barun, Journal of Bacteriology 1989, 171: 5117-5126].

An exemplary method for purifying a histidine tagged pore-forming polypeptide is described in protocol of Locher and Rosenbush Eur J Biochem 1997 and Nallani et al. 2006, [J Biotechnology 123, 50-9 (2006).]. Briefly, an outer membrane fraction comprising the polypeptide of the invention is solubilized in 1% Octyl Glucoside or 1% Octly-polyoxoethylene or 0.5% Dodecyl Maltoside (Locher 1997) by shaking for 1 hour at 37° C. and then for 10 hours at 12° C. The soluble fraction is then centrifuged for 15 minutes at 4° C. at 50,000 g and the supernatant containing the engineered pore-forming polypeptide is passed through an affinity chromatography column containing Talon Metal Affinity Resin (Clontech, Cat 635502) and eluted with 150 mM imidazole solution. The protein may be concentrated with Amicon ultrafiltration cell PM 30 and dialyzed against Hepes Buffer.

As mentioned, the pore-forming polypeptides of the present invention may be inserted into the lipid layer of an encapsulating particle such that it forms a protease-activatable pore through the lipid layer.

Thus, according to another aspect of the present invention there is provided a composition of matter, comprising an encapsulating particle and the isolated polypeptide of the present invention wherein the encapsulating particle comprises at least one lipid layer, and a compartment surrounded by the lipid layer, and further wherein the isolated polypeptide is positioned such that it is capable of forming a pore through the lipid layer in a presence of the protease.

The present invention also provides for a method of producing a drug delivery system, comprising encapsulating the isolated polypeptide described herein with an encapsulating particle, wherein said encapsulating particle comprises at least one lipid layer, and a compartment surrounded by said lipid layer, and further wherein the isolated polypeptide is positioned such that it is capable of forming a pore through said lipid layer in a presence of said protease.

As used herein, the phrase "encapsulating particle" refers to an entity that is characterized by the presence of one or more walls or membranes formulated from lipids and/or fatty acids that form one or more internal voids. The walls or membranes may be concentric or otherwise. The walls or membranes of vesicles may be substantially solid (uniform), or referred to as, for example, liposomes, lipospheres, nanoliposomes, particles, micelles, bubbles, microbubbles, microspheres, nanospheres, nanostructures, microballoons, microcapsules, aerogels, clathrate bound vesicles, hexagonal/cubic/hexagonal II phase structures, and the like.

The lipids used to formulate the particles of the present invention are generally amphipathic lipids having both hydrophobic tail groups and polar head groups. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. A particle-forming lipid for use in the present invention is any conventional lipid possessing one of the characteristics described above.

The particle-forming lipids of this type are preferably those having two hydrocarbon tails or chains, typically acyl groups, and a polar head group. Included in this class are the phospholipids, such as phosphatidylcholine (PC) or lecithin, phosphatidylethanolamine (PE), phosphatidyl-N-methylethanolamine (PE-Me), phosphatidyl-N,N-dimethylethanolamine (PE-diMe), phosphatidyl serine (PS), phosphatidic acid (PA), phosphatidylglycerol (PG), a polyol-containing phosphatide, and phosphatidylinositol (PI), where the two hydrocarbon chains are typically between about 14-22 carbon atoms in length, and have varying degrees of unsaturation.

Other lipids which may be used to formulate the particles of the present invention include 1-monopalmitoleoyl-rac-glycerol (MP), Palmitoyl lysophosphatidylcholine (PLPC), and 1y 1-monooleoyl-rac-glycerol (MO).

The above-described lipids and phospholipids whose acyl chains have a variety of degrees of saturation can be obtained commercially, or prepared according to published methods.

Lipids for use in the present invention may be relatively "fluid" lipids, meaning that the lipid phase has a relatively low gel-to-liquid-crystalline phase transition temperature, e.g., at or below room temperature, or alternately, relatively "rigid" lipids, indicating that the lipid has a relatively high gel-to-liquid-crystalline phase transition temperature, e.g., at temperatures up to about 50° C. As a general rule, the more rigid, i.e., saturated lipids, contribute to greater membrane rigidity in the lipid bilayer structure, and thus to more stable drug retention after active drug loading. Preferred lipids of this type are those having phase transition temperatures above about 37° C.

The particles may additionally include lipids that can stabilize a particle composed predominantly of phospholipids, such as cholesterol in a mole ratio of 25 to 45 mole percent.

According to one embodiment the lipid layer of the encapsulating agents of the present invention comprise poly(acrylic acid) and/or poly(N-isopropylacrylamide).

According to one embodiment the lipid layer of the encapsulating agents of the present invention comprise phosphatidic acid and/or L-α-dimyristoyl phosphatidic acid.

According to one embodiment, the encapsulating particles of this aspect of the present invention are liposomes.

As used herein the term "liposomes" refers to fully closed carrier molecules comprising a spherical lipid membrane which itself is in a liquid crystalline phase or a liquid gel phase, in which an entrapped liquid volume is contained. The two liquid phases are immiscible. Thus, liposomes of the present invention, similar to membranes of cells, are in an entirely gel/liquid state and/or liquid crystal state and not in a solid state. Liposomes include niosomes, transfersomes, emulsions, foams, micelles, liquid crystals, phospholipid dispersions, lamellar layers and the like.

Liposomes used in the invention preferably contain between 30-75 percent phospholipids, preferably phosphatidylcholine (PC), 25-40 percent cholesterol, and 0-20 percent polymer-derivatized lipid, expressed on a molar percent basis.

The liposomes may optionally include a coating or a graft of a hydrophilic polymer chain, for extended circulation lifetime in the bloodstream (see U.S. Pat. No. 5,130,556). Such liposomes are typically prepared by including in the vesicle-forming lipid, 1-20 mole percent of a diacyl-chain lipid, e.g., a phospholipid, derivatized with the hydrophilic polymer, e.g., polyethylene glycol (PEG) having a molecular weight between 1-10 Kdaltons, preferably 2-5 Kdaltons. Methods for preparing PEG-derivatized phospholipids are detailed, for example, in the above cited U.S. Pat. No. 5,013,556.

One of the most desirable features of PEG is its approval by the U.S. Food and Drug Administration (FDA) for in-vivo administration. Ample guidance for selecting and utilizing PEG for practicing the method of the present invention is available in the literature of the art [for general guidance, refer, for example, to Zalipsky, S., Harris, J. M. 1997. Introduction to Chemistry and Biological Applications of Poly (ethylene glycol). Poly(ethylene glycol) Chemistry and Biological Applications. American Chemical Society, San Francisco, Calif. (p. 1-11); for guidance for covalently attaching PEG to molecules, such as therapeutic nucleic acids and polypeptides, refer, for example, to: Molineux G., 2002. Cancer Treat Rev. 28 Suppl A:13-6; Harris J M. and Chess R B., 2003. Nat Rev Drug Discov. 2:214-21; Sato H., 2002. Adv Drug Deliv Rev. 54:487-504; Roberts et al., 2002. Adv Drug Deliv Rev. 54:459-76).

Other hydrophilic polymers which may be suitable include polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose. Phospholipid polymer conjugates of these polymers are described in WO 94/02271, published Sep. 3, 1994.

One exemplary "rigid" polymer-grafted liposome formulation is formed of polyethylene glycol conjugated phosphatidylethanolamine, PEG-PE, hydrogenated soy phosphatidylcholine (HSPC) and cholesterol in a weight ratio of 1:3:1. Two exemplary polymer coated fluid liposome compositions contain the components PEG-PE, egg phosphatidylcholine (EPC), and cholesterol, in corresponding molar ratios of 6:56:38 and 6:62:32.

Another plausible approach to stabilize and create 'stealth' liposomes utilizes cholesterol terminated polyacrylic acid (Chol-PAA). Since it is easily inserted and cross-linked with 2,2'-ethylenedioxy-bis ethylamine on the surface of a liposome, this results in a very stable polymer-cage, as described in Lee, S. M., Chen, H., Dettmer, C. M., O'Halloran, T. V. & Nguyen, S. T. Polymer-caged liposomes: a pH-responsive delivery system with high stability. J Am Chem Soc 129, 15096-7 (2007).

Another approach to stabilizing liposomes is with the use of naturally occurring hyaluronic acid. Hyaluronan provides long term circulation as well as targeting of overexpressed hyaluronan receptors CD44 and RHAMM. Dan Peer and Rimona Margalit Tumor-Targeted Hyaluronan Nanoliposomes Increase the Antitumor Activity of Liposomal Doxorubicin in Syngeneic and Human Xenograft Mouse Tumor Models Neoplasia. 2004 July; 6(4): 343-353.

Sterically shielded lipids such as ganglioside-$GM_1$ and phosphatidylinositol may also be used to generate 'stealth' liposomes.

The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. In a typical procedure, a mixture of liposome-forming lipids is dissolved in a suitable organic solvent and evaporated in a vessel to form a thin film. The film is then covered with an aqueous medium containing the solute species that will form the aqueous phase in the liposome interior spaces, in the final liposome preparation. The lipid film hydrates to form multilamellar vesicles (MLVs) having heterogeneous sizes typically between about 0.1 to 10 microns. Liposomes can be reduced in size by various techniques known in the art such as, extrusion or sonication.

In the general case, the liposomes are prepared in a solution containing a weak acid salt, such as sodium or calcium acetate, sodium or calcium formate, or other suitable salt of a weak organic acid, such as salts of propanoic, butanoic, or pentanoic acid, and derivatives thereof, as defined in Section I. The weak acid is one which, in its uncharged or undissociated form, is readily able to permeate the transmembrane barrier of the liposomes. The acid salt also preferably has a high solubility in water, e.g., greater than about 300 mg/ml. The hydration medium is preferably at least 50 mM weak acid salt, and typically between 50-300 mM. The medium is adjusted, e.g., by addition of acid, to a pH of between 5 and 7, but contains no additional buffering species.

After liposome formation, the vesicles may be sized to achieve a size distribution of liposomes within a selected range, according to known methods. The liposomes are preferably uniformly sized comprising a diameter of less than 150 nm. An exemplary selected size range may be between 0.04 to 0.15 µm. Small unilamellar vesicles (SUVs), which are single-walled vesicles typically in the 0.04 to 0.08 µm range, can be prepared by extensive sonication or homogenization (Martin, et al., 1990) of the liposomes.

Homogeneous sized liposomes having sizes in a selected range between about 0.08 to 0.4 microns, e.g., 0.07-0.12 microns, can be readily produced by extrusion through defined pore-size membranes, e.g., polycarbonate membranes, having defined pore size membranes with selected pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane.

The sizing is preferably carried out in the original lipid-hydrating buffer, so that the liposome interior spaces retain this medium throughout the initial liposome processing steps.

As mentioned, the encapsulating particle of this aspect of the present invention may also be a mesophase (cubic-phase). Cubic-phases are biodegradable, continuous lipid bilayers that are isotropically curved in three-dimensional space, in a manner that separates between two tunnel-like aqueous compartments (Luzzati, V. 1997 Curr. Opin. Struct. Biol. 7, 661-668). The aqueous compartments of these lipidic phases can accommodate solutes as large as lysozyme (Rummel, G. et al., 1998 J. Struct. Biol. 121, 82-91), making cubic phases a potential drug-carrier system. The cubic phases can be constructed out of various lipids mixtures including (but not limited to) 1-monopalmitoleoyl-rac-glycerol (MP), Palmitoyl lysophosphatidylcholine (PLPC), and preferably 1-monooleoyl-rac-glycerol (MO). When controlling the temperature and lipid/water content one can adjust the cubic-phase types as described in the phase diagrams in Caffrey M. J Struct Biol. 2003 April; 142(1):108-32. Review.

Any method may be used to insert the pore-forming polypeptides into the encapsulating particles of the present invention so long as it does not interfere with the required properties of the polypeptide. Preferably, the pore-forming polypeptide is inserted such that at least one protease cleavage site faces the outside of the encapsulating particle.

For example, reconstitution of a pore-forming polypeptide into a liposome may be performed following the procedure of Plancon, L., Chami, M. & Letellier, L. Reconstitution of FhuA, an *Escherichia coli* outer membrane protein, into liposomes. Binding of phage T5 to Fhua triggers the transfer of DNA into the proteoliposomes. J Biol Chem 272, 16868-72 (1997)., incorporated herein by reference. In brief, liposomes (e.g. 5 mM) are incubated with Octyl glucoside (e.g. 22 or 45 mM) for about 30 minutes. The pore-forming polypeptide (e.g. FhuA; 35 µg) is added and the detergent concentration adjusted to either 22 or 45 mM. The detergent is then adsorbed onto $SM_2$ Bio-Beads and at a concentration of 80 mg of wet Bio-Beads/ml, the suspension is shaken gently. 3 hours later, a second portion of the same amount of Bio-Beads is added and the suspension is shaken overnight at 4° C. Proteoliposomes are removed gently after decanting the Bio-Beads.

Other methods for the covalent attachment of the pore-forming polypeptide to the encapsulating particles include the use of an amide, ester, or ether bond, streptavidin and biotin (see, for instance, U.S. Pat. No. 5,171,578), and activation of a polypeptide with carbodiimide followed by coupling to the activated carboxyl groups (U.S. Pat. No. 5,204,096)). Other examples of methods that can be used to covalently bind a polypeptide to a lipid are disclosed in U.S. Pat. No. 5,258,499.

The encapsulating particles may optionally be prepared to contain additional surface groups, such as antibodies or antibody fragments, small effector molecules for interacting with cell-surface receptors, antigens, and other like compounds for achieving desired target-binding properties to specific cell populations. Here the lipid component included in the encapsulating particles would include either a lipid derivatized with the targeting molecule, or a lipid having a polar-head chemical group that can be derivatized with the targeting molecule in preformed particles, according to known methods.

Ample guidance regarding surface markers specifically overexpressed in diseases such as cancer, and antibodies specific for such surface markers is provided in the literature of the art (for example, refer to: A M Scott, C Renner. "Tumour Antigens Recognized by Antibodies." In: Encyclopedia of Life Sciences, Nature Publishing Group, Macmillan, London, UK, wwwdotelsdotnet, 2001).

Diseases associated with a target cell/tissue specifically displaying a growth factor receptor/TAA surface marker which are amenable to treatment by the method of the present invention include, for example, some of the numerous diseases which specifically display growth factor receptors/TAAs, such as EGF receptor, platelet derived growth factor (PDGF) receptor, insulin like growth factor receptor, vascular endothelial growth factor (VEGF) receptor, fibroblast growth factor (FGF) receptor, transferrin receptor, and folic acid receptor. Specific examples of such diseases and the growth factor receptors/TAAs which these specifically display are listed in Table 6 below.

Examples of therapeutic agents include, but are not limited to small molecule agents (e.g. those that are less than 1000 kDa), organic compounds, inorganic compounds, metal ions, polypeptides (e.g. enzymes or enzyme inhibitors), non-ribosomal polypeptides, polyketides, peptidomimetics and polynucleotides. According to one embodiment, the therapeutic agent is a chemotherapeutic agent including but not limited to fluoropyrimidines; pyrimidine nucleosides; purines; antifolates, platinum analogs; electrophilic alkylating agents; anthracyclines/anthracenediones; podophyllotoxins; camptothecins; hormones and hormonal analogs; enzymes, proteins, and antibodies, vinca alkaloids, taxanes and epothilones. Other contemplated therapeutic agents include viruses.

Specific examples of chemotherapeutic agents include Doxorubicin, Camptothecin, Paclitaxel, and Palatinate.

Examples of diagnostic agents include, for instance, positive or negative contrast agents that can be used for imaging such as gadolinium or magnetic particles and fluorescent dyes. Preferably, the internal compartment of the encapsulating particle also includes a pharmaceutically acceptable carrier, as further described herein below. The internal compartment may include a compound that inhibits the activity of the protease that cleaves the pore-forming polypeptide present on the surface of the liposome. For example, in those aspects of the invention where the trigger polypeptide present on the surface of the liposome is cleaved by gelatinase-A and/or gelatinase-B, an inhibitor of gelatinase-A and/or gelatinase-B activity may be used. Examples of gelatinase-A and gelatinase-B inhibitors are known. An example of such a compound is H-$Cys^1$-Thr-Thr-His-Trp-Gly-Phe-Thr-Lue-$Cys^{10}$-OH (cyclic: 1->10) (SEQ ID NO:23).

The present invention contemplates at least two possible mechanisms for releasing the inner contents of the encapsulating particle. In one embodiment, the pore-forming polypeptide generates a pore wide enough (in the presence of

TABLE 6

| Receptor* | Malignancy type | Review reference |
| --- | --- | --- |
| EGF receptor | Malignant glioma, glioblastoma, head and neck, breast, colon, lung, prostate, kidney, ovary, brain, pancreas, bladder | Kim, E. S. et al., 2001. Curr Opin Oncol 13, 506-13; Kuan et al., 2000. Brain Tumor Pathol. 2000; 17: 71-8 |
| PDGF receptor | Brain, prostate | George, D., 2001. Semin Oncol 28, 27-33 |
| IGF receptor | Breast, lung, colon, prostate | Wang, Y., and Sun, Y., 2002. Curr Cancer Drug Targets 2, 191-207 |
| VEGF receptor | Solid tumors, acute and chronic leukemias, myeloproliferative diseases, multiple myeloma, non-Hodgkin's lymphomas, and Hodgkin's disease | Rosen, L. S., 2001. Cancer J 7 Suppl 3, S120-8; Giles, F. J., 2001. Oncologist 6, 32-9 |
| FGF receptor | Melanoma, Caposi sarcoma, pancreas | Lappi, D. A., 1995. Semin Cancer Biol 6, 279-88 |
| Transferrin receptor | Leukemia, brain, colon, kidney, bladder | Singh, M., 1999. Curr Pharm Des 5, 443-51 |

*Abbreviations: EGF—epidermal growth factor, PDGF—platelet derived growth factor, IGF—insulin like growth factor, VEGF—vascular endothelial growth factor, FGF—fibroblast growth factor.

This interior compartment includes a liquid that is aqueous. The compartment also includes one or more compounds present in the liquid. The compound may be, for instance, a liquid, a solid that is dissolved in the liquid, or a solid that is suspended in the liquid.

The internal compartment of the particles may be filled with a wide variety of materials including, for example, therapeutic agents, diagnostic agents, water, oil, gases, gaseous precursors, liquids, fluorinated compounds or liquids, liquid perfluorocarbons, liquid perfluoroethers and/or other materials.

a protease) to allow the contents of the encapsulating particle to be released. In another embodiment, the pore-forming polypeptide generates a pore wide enough (in the presence of a protease) to allow water to filter into the encapsulating particle by osmosis thereby bursting it open and allowing the subsequent release of the inner contents.

Since the encapsulating particles may be filled with therapeutic agents, the particles may be used to treat a disease.

Thus, according to another aspect of the present invention, there is provided a method of treating a disease associated with an up-regulation of a protease in a subject in need thereof, the method comprising administering to the subject a therapeutically effective amount of the above described composition of matter.

Exemplary diseases that are associated with an up-regulation of a protease include, but are not limited to cancer (including solid tumors), gouty arthritis, inflammatory bowel disease (ulcerative colitis), abdominal aortic aneurysms, quiescent Crohn's Disease, glaucoma, and sunlight induced premature skin aging. For example, Vartak et al. Journal of Drug Targeting, January 2007; 15(1): 1-20 (which is herein incorporated by reference in its entirety) review the significance of MMPs in various pathologies including but not limited to, Arthritis, Inflammation, innate immunity, Cancer, Angiogenesis, Cardiovascular diseases, Cerebrovascular diseases, Pulmonary diseases, Ocular diseases, Gastrointestinal diseases, and Oral diseases. See also Example 8 of the Examples section which follows.

As used herein, the term "cancer" refers to a disease or disorder resulting from the proliferation of oncogenically transformed cells.

Exemplary cancers which may be treated according to the present invention include, but are not limited to tumors of the gastrointestinal tract (colon cancer, rectum cancer, anal region cancer, colorectal cancer, small and/or large bowel cancer, esophageal cancer, stomach cancer, pancreatic cancer, gastric cancer, small intestine cancer, adenocarcinoma arising in the small intestine, carcinoid tumors arising in the small intestine, lymphoma arising in the small intestine, mesenchymal tumors arising in the small intestine, gastrointestinal stromal tumors), gallbladder carcinoma, Biliary tract tumors, prostate cancer, kidney (renal) cancer (e.g., Wilms' tumor), liver cancer (e.g., hepatoblastoma, hepatocellular carcinoma), hepatobiliary cancer, biliary tree cancer, tumors of the Gallbladder, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian cancer, cervical cancer, cancer of the vagina, cancer of the Vulva, lung cancer (e.g., small-cell and non-small cell lung carcinoma), nasopharyngeal, breast cancer, squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic, cutaneous T-cell lymphoma, primary central nervous system lymphoma), gliomas, medullary thyroid carcinoma, testicular cancer, brain and head/neck cancer, gynecologic cancer, endometrial cancer, germ cell tumors, mesenchymal tumors, neurogenic tumors, cancer of the bladder, cancer of the ureter, cancer of the renal pelvis, cancer of the urethra, cancer of the penis, cancer of the testis, cancers of the uterine body, endometrial carcinoma, uterine sarcoma, peritoneal carcinoma and Fallopian Tube carcinoma, germ cell tumors of the ovary, sex cord-stromal tumors, cancer of the endocrine system, thyroid tumors, medullary thyroid carcinoma, thyroid lymphoma, parathyroid tumors, adrenal tumors, pancreatic endocrine tumors, sarcomas of the soft tissue and bone, benign and malignant mesothelioma, malignant peritoneal mesothelioma, malignant mesothelioma of the Tunica Vaginalis Testis, malignant mesothelioma of the Pericardium, skin cancer, cutaneous melanoma, intraocular melanoma, neoplasms of the central nervous system, medulloblastomas, meningiomas, peripheral nerve tumors, Pineal region tumors, pituitary adenomas, craniopharyngiomas, acoustic neuromas, Glomus Jugulare tumors, Chordomas and Chondrosarcomas, Hemangioblastomas, Choroid Plexus Papillomas and Carcinomas, spinal axis tumors, leukemia, and chronic leukemia.

The term "subject" refers to animals, typically mammals, including human beings.

As mentioned, the particles of the present invention may be administered to the patient per se or as part of an individual pharmaceutical composition.

As used herein a "pharmaceutical composition" refers to a preparation of the encapsulating particles described herein comprising one or more therapeutic agent, together with other chemical components such as pharmaceutically suitable carriers and excipients. The purpose of a pharmaceutical composition is to facilitate administration of a compound to a subject.

Herein, the term "active ingredient" refers to the encapsulating particles comprising at least one or more therapeutic agents, accountable for the biological effect.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the particles of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the particles can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the particles may take the form of tablets or lozenges formulated in conventional manner.

For administration by inhalation, the particles of the present invention may be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The particles described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active agents to allow for the preparation of highly concentrated solutions. Alternatively, the active ingredient may be in powder form for constitution with a suitable vehicle, e.g., sterile, pyrogen-free water, before use.

The particles of the present invention may also be formulated in rectal compositions such as suppositories or retention enemas, using, e.g., conventional suppository bases such as cocoa butter or other glycerides.

Alternately, one may administer the particles of the present invention in a local rather than systemic manner, for example, via injection of the pharmaceutical composition directly into a tissue region of a patient.

Thus for example, the particles of the present invention may be administered directly into the tumor.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose.

Determination of a therapeutically effective amount of each of the active agents is well within the capability of those skilled in the art, especially in light of the detailed disclosure provided herein.

For any of the active agents used in the methods of the invention, the therapeutically effective amount or dose can be estimated initially from activity assays in cell cultures and/or animals.

Below is a list of animal models and animal cell lines that can be used to ascertain the therapeutically effective amount of the active agents of the present invention.

Tumor Formation in Transgenic Mice Overexpressing an Oncogene

A transgenic mouse model for cancer (e.g., breast cancer) such as the erb model (Shah N., et al., 1999, Cancer Lett. 146: 15-2; Weistein E J., et al., 2000, Mol. Med. 6: 4-16) or MTV/myc model (Stewart T A et al., 1984, Cell, 38: 627-637), the c-myc model (Leder A., et al., 1986, Cell, 45:485-495), v-Ha-ras or c-neu model (Elson A and Leder P, 1995, J. Biol. Chem. 270: 26116-22) can be used to test the ability of the active agents, both individually and in combination to suppress tumor growth in vivo.

Tumor Formation in Mice Administered with Cancerous Cell Lines

For the formation of solid tumors, athymic mice can be injected with human or animal (e.g., mouse) cancerous cells such as those derived from breast cancer, ovarian cancer, prostate cancer or thyroid cancer, and following the formation of cancerous tumors the mice can be subjected to intra-tumor and/or systemic administration of the active agents of the present invention, both individually and in combination.

Toxicity and therapeutic efficacy of the agents described herein both alone and in combination can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

Side effects of each of the agents of the present invention at doses which are effective at treating cancer may be assayed using standard assays known in the art.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide local levels of the active agents which are sufficient to maintain the cytotoxic activity, termed the minimal effective concentration (MEC). The MEC will vary for each preparation, but can be estimated from in vitro and/or in vivo data, as described hereinabove. Dosages necessary to achieve the MEC will depend on individual characteristics and route of administration. HPLC assays or bioassays can be used to determine local concentrations.

Dosage intervals can also be determined using the MEC value. Preparations should be administered using a regimen, which maintains local levels above the MEC for 10-90% of the time, preferable between 30-90% and most preferably 50-90%.

The amount of a composition to be administered will, of course, be dependent on the subject being treated, the severity of the pain, the manner of administration, the judgment of the prescribing physician, etc.

Compositions of the present invention may, if desired, be presented in a pack or dispenser device, such as a FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the active agents of the invention formulated in a compatible pharmaceutical carrier may also be prepared, placed in an appropriate container, and labeled for the treatment of a particular disease, such as cancer.

It is expected that during the life of a patent maturing from this application many relevant encapsulating particles will be developed and the scope of the term "encapsulating particle" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Engineering of FhuA:

The engineering of the prototypic pore-forming polypeptide was based on the 'X'-ray crystal structure of a histidine-tagged FhuA, which was previously determined at atomic resolution (Swiss-Prot primary accession no. P23979; RCSB Protein Data Bank (PDB) ID code 1FCP). Using Deepview/Swiss PDB-Viewer 3.7 and PyMOL, the His$_6$-tagged FhuA was carefully inspected and mutated in silico. Ten potential MMP-7 cleavage sites were inserted into the extracellular loops and the cork, these include 68 amino acid mutations for creating MMP cleavage sites and 5 mutations assigned to preventing clashes between the newly designed loops. The sequence of the in silico mutated FhuA$_{7/10}$-1 was aligned with the sequence of FhuA (1FCP), and then was submitted for automated comparative protein modeling via the SWISS-PROT alignment interface (http://swissmodeldotexpasydotorg/SWISS-MODELdothtml) [Guex, N. & Peitsch, M. C. Electrophoresis 18, 2714-23 (1997); Schwede, T., et al., Nucleic Acids Res 31, 3381-5 (2003)]. The rms difference (rmsd) between the backbone (2,820 atoms) of the FhuA structure (1FCP) and the mutated FhuA$_{7/10}$-1 was 0.08 Å. Energy minimizations of the FhuA$_{7/10}$-1 was performed with GROMOS96 (free energy reached −31,719 kjoul/mol). The sequences of the wild-type and mutated proteins are provided in Table 7 herein below.

TABLE 7

| Protein | Amino acid sequence | Polynucleotide sequence |
| --- | --- | --- |
| Wild-type FhuA | SEQ ID NO: 1 | SEQ ID NO: 2 |
| Wilt-type FhuA with histidine tag | SEQ ID NO: 3 | SEQ ID NO: 4 |
| FhuA$_{7/10}$-1 with histidine tag | SEQ ID NO: 5 | SEQ ID NO: 6 |
| FhuA$_{7/10}$-1 | SEQ ID NO: 7 | SEQ ID NO: 8 |
| Wild Type OprD | SEQ ID NO: 9 | SEQ ID NO: 10 |
| Oprd-D15 signal Peptide | SEQ ID NO: 11 | SEQ ID NO: 12 |
| OprD-D15-mutPL2b | SEQ ID NO: 13 | SEQ ID NO: 14 |
| OprD-D15-mutLa3 | SEQ ID NO: 15 | SEQ ID NO: 16 |

Transfection of Cultured Cells and Cell Harvesting:

Human embryonic kidney (HEK-293T) cells were cultured and transfected by using the calcium phosphate precipitation technique with expression vectors (pMT3)[53] carrying the cDNA insert encoding the engineered FhuA (FhuA$_{7/10}$-1). 10-20 μg DNA was used per 100-mm plate. Two to three days following transfection, when the cells started to lose their normal morphology and became round shaped, they were harvested with phosphate buffered saline (PBS) containing 5 mM EDTA and protease inhibitor cocktail (1 μl/3ml solution; Sigma-Aldrich, Israel, cat. #P-8340). Cells were then centrifuged at 800 g for 10 min and the pellet was frozen in liquid nitrogen and stored at −80° C.

Membrane Preparation:

Harvested cells were defrosted on ice and ice cold PBS was added with protease inhibitor cocktail (concentration as above). These cells were then homogenized with either glass-glass hand homogenizer or teflon-glass electric homogenizer (Heidolph 50110). The homogenate was centrifuged for 10 min at 800 g in order to remove nuclei and large debris; this step was repeated twice more on the pellet.

Supernatant was collected and centrifuged at 15,000 g for 40 minutes. After discarding the supernatant, the pellet was re-homogenized and centrifuged again for 40 minutes at 15,000 g, and finally re-suspended in PBS with or without cocktail and stored in liquid nitrogen.

Azocoll Spectrophotometry:

Azocoll, a general proteolytic substrate made from collagen with an embedded azo dye, yields a red color when cleaved, with an absorbance at 520 nm. 0.2 mg of Azocoll (Calbiochem, cat #194933) was incubated with 3.58 U of human matrix metalloproteases seven (MMP-7, Calbiochem, cat #444270) in PBS for 15 hours at 37° C. in the presence and absence of protease inhibitor cocktail (Sigma, cat #P8349). Measurements were carried out using the Ultrospec 2100 pro (Amersham Biosciences).

Cleavage by MMP and Western Blotting:

Membrane aliquots of 100-250 μl were washed twice with PBS, protease inhibitor cocktail, and 400 mM NaCl, re-homogenized and centrifuged for 30 minutes at 18,000 g, followed by three washes with PBS with or without cocktail.

Human MMP-7 was added at 0.25 μl (3.85 units) per 20 ul membranes for various times at 37° C. Samples were analyzed on a 10% SDS-PAGE, transferred onto nitrocellulose or PVDF paper, blocked with blocking buffer (5% Bovine Serum Albumin, Sigma, cat. #A2153 and 2% Blotting Milk, Bio-Rad, cat. #1706404) and blotted for 2 hours with anti-His$_5$ monoclonal antibody (Novagen, cat. #70796; diluted 1:1000, in blocking buffer). After six washes, which included three ten-minute washes with PBS and 0.1% Tween 20 (Sigma, cat. #P1379) and another three ten-minute washes with PBS alone, goat anti-Mouse HRP antibody (Calbiochem, cat. #401215) was added at a dilution of 1:20,000 in blocking buffer for 2 hours. After six washes, as above, the film was developed with ECL reagent (Biological Industries, cat #20-500-120). The film was scanned with a simple Canon scanner (Canoscan LiDE 30) and densitometry was performed using Adobe Photoshop 7.0 ME by inverting the image colors, tracing the band and measuring the mean gray value.

Confocal Microscopy:

HEK293T cells were transfected with 2 μg of FhuA$_{7/10}$-1 by the calcium phosphate method, in glass bottom microwell dishes (MatTek, cat. #P35G-1.5-14-C), where the glass was coated with 20 μg/ml poly-L-lysine. Three days after transfection, primary anti-His$_5$ antibodies (mouse, Calbiochem, cat. #70796) were added at 1:1000 dilution directly to the cell culture with 50 mM Hepes for stabilizing the pH, and cells were further incubated overnight at 4° C. Medium was washed out 3 times for 10 minutes with 5 mg/ml BSA dissolved in a solution of 140 mM NaCl, 2.8 mM KCl, 10 mM CaCl$_2$, 10 mM glucose, 10 mM HEPES, and 5 mM NaOH, pH 7.35. Secondary antibody (rhodaminylated goat anti-mouse IgG, H & L chains, Calbiochem cat. #401245) was added at 1:100 dilution and again washed with same solution as before, 3 times for 10 minutes. The Zeiss-LSM510 was used for confocal microscopy.

Electrophysiology in HEK293T Cells:

HEK293T cells were plated on poly-L-lysine coated glass cover slips (20 µg/ml) and transfected with 2 µg DNA (calcium phosphate technique). Ionic currents were observed upon addition of MMP-7 at 23° C. For that, voltage-clamp recordings in HEK cells were performed, using the whole-cell configuration of the patch-clamp technique. Signals were amplified using an Axopatch 200B patch-clamp amplifier (Molecular Devices, Sunnyvale, Calif.), sampled at 2 kHz and filtered at 800 Hz via a 4-pole Bessel low pass filter. Data were acquired using pClamp 10.0 software (Molecular Devices) in conjunction with a DigiData 1440A interface (Molecular Devices). The patch pipettes were pulled from borosilicate glass (Warner Instrument Corp, USA) with a resistance of 4-8 M. For current recordings in HEKcells, the intracellular pipette solution contained (in mM): 130 CsCl, 4 MgCl$_2$, 4Na$_2$ATP, 1 EGTA, 10 HEPES, adjusted with CsOH to pH 7.35 (290 milliosmolar). The extracellular solution contained (in mM): 140 NaCl, 2.8 KCl, 10 CaCl$_2$, 2 MgCl$_2$, 10 glucose, 10 HEPES, adjusted with NaOH to pH 7.35 (310 milliosmolar). Series resistances (3-20 MΩ) were compensated (75-90%) and periodically monitored.

Example 1

Engineering of a Pore-Forming Polypeptide (FhuA$_{7/10}$-1)

In order to successfully engineer a cleavage site motif into the FhuA—such that the protein will still be expressed—each amino acid mutation was considered carefully, attempting not to stray from the biochemical properties of each wild-type amino acid. Note, that drastically changing an amino acid may impair its folding and subsequently its expression.

To avoid such a situation, the bond networks of the native and substituting amino acids was considered. For example, native amino acid side-chains which face into the protein may interact via H-bonds with other amino acids, therefore, the mutated amino acid must attempt to keep this same interaction. To this end, the volume of the amino acid's side chain, its charge, and overall chemical structure (aromatic side-chains in particular) were kept similar. Hydrophobicity of amino acid side chains located at the perimeter of the barrel (FIGS. 1A-J) also play an important role in determining the FhuA's placement in the lipid bi-layer; therefore, polar and non-polar side chains were also kept constant during mutagenesis. Proline containing loops were selected for mutagenesis since they are contained in MMP-7 cleavage sites.

Seventy three native amino acids were replaced in order to introduce ten cleavage sites in loops and 13 strands of FhuA. Five site-specific mutations were performed in order to maintain the correct 3-D structure of the polypeptide. Prior to in silco mutagenesis, the overall free energy of the FhuA (PDB ID code 1FCP) was −26,481 kjoul/mol as calculated by GROMOS96, in vacuo. Following mutagenesis, the free energy of the $FhuA_{7/10}$-1 (FIGS. 1A-F) went down to −31,719 kjoul/mol. The resulting free energy is more negative, indicating that there were neither distortions in the backbone nor in the side chains. In the final structural model, no clashes took place between amino acids and the backbone, nor between side chains of amino acids. Most of the ten cleavage sites are solvent accessible and some are located at secondary-tier sites including the cork. The Doxorubicin that was modeled into the $FhuA_{7/10}$-1 (FIGS. 1B & 1G) is approximately the same size as the Ferrichrome (FIGS. 1C & 1H), which is naturally transported into bacteria by the wild-type FhuA. Therefore, Doxorubicin will have sufficient space to diffuse through the channel after complete cleavage. FIGS. 1D, 1I, 1E and 1J show the Connolly Surface of the $FhuA_{7/10}$-1, where solvents contact the surface of the molecule at each possible position. This affirms that the cleavage sites are on the surface and are accessible to MMP cleavage activity. FIGS. 1A, 1F, 1D, 1I, 1E and 1J also indicate that, prior to cleavage, the extracellular loops and cork of the engineered $FhuA_{7/10}$-1 will completely obstruct all possible leakage of Doxorubicin after loading it into liposomes, because the entire channel (formed by the β-barrel) is occupied.

Example 2

The Engineered $FhuA_{7/10}$-1 Folds Properly and Arrives at the Cell Surface To assess whether the engineered $FhuA_{7/10}$-1 folds properly, human embryonic kidney cells (HEK293T) were transfected with DNA encoding the $FhuA_{7/10}$-1. Living cells expressing the $FhuA_{7/10}$-1 were able to bind anti-$His_5$ antibodies (FIGS. 2A-F) and TALON beads coated with cobalt that displays a high affinity to the histidine tag (FIG. 3). These observations indicate that the many mutations did not affect the translation, folding, and cell-surface expression of the $FhuA_{7/10}$-1. The finding that the His tag is facing the extracellular milieu indicates that the transmembrane topology of the protein is similar to that of the wild-type.

Example 3

The Membrane-Integrated Pore-Forming Polypeptide is Accessible to Cleavage by Human MMP-7

The capacity of human MMP-7 to cleave the engineered $FhuA_{7/10}$-1 was examined in membrane preparations where the pore-forming polypeptide is integrated and folded in its natural environment, within the lipid bilayer. For that, HEK293T cells were transfected with a plasmid DNA encoding the engineered $FhuA_{7/10}$-1, and membranes were prepared as described in "Materials & Methods". It should be noted that membrane preparations might contain residual proteolytic activity that was procedurally inhibited by addition of a mixture of protease inhibitors. Therefore, as a preliminary set of experiments, the effect of particular protease inhibitors was examined on the activity of human MMP-7. FIG. 4 shows that protease inhibitor cocktail has no detrimental affect on MMP-7 activity. This inhibitor cocktail includes AEBSF, Aprotinin, Bestatin hydrochloride, E-64, Leupeptin hemisulfate salt, Pepstatin A, and does not include inhibitors of metalloproteinases.

FIG. 5A (lane 1, indicated by 'a') shows that the uncleaved $FhuA_{7/10}$-1 migrates as a ~81 kDa polypeptide, as is the case of the wild type FhuA. Incubation of the membranes with human MMP-7 for 30 minutes at 37° C. resulted in the appearance of ~57- and ~37-kDa bands (FIG. 5A, lane 3 compared to lane 2, indicated by 'b' and 'c'). It was also evident that some degradation takes place also in the absence of MMP-7. This might indicate the presence of inherent proteolytic activity in the membrane preparation. Therefore, the present inventors examined the effect of the aforementioned protease inhibitor cocktail on this plausible inherent activity and on the activity of MMP-7. Comparison of lanes 4 (without MMP-7) and 5 (with MMP-7) in FIG. 5A shows that the inhibitor cocktail used, does not inhibit the activity of MMP-7 and slightly inhibits the proteolytic activity inherent to the preparation. Longer incubation periods virtually gave the same results (FIG. 5A, lanes 8 & 9). One cannot exclude the possibility that some proteolytic activity takes place prior to cell harvesting owing to over expression of FhuA$_{7/10}$-1 in the cells, as well as due to some metallo-proteolytic activity naturally produced by HEK cell. Such inherent proteolytic activity can easily be seen in membranes prepared of over-expressing cells (FIG. 5B lane 10, compared to cleavage by exogenously added MMP-7).

FIG. 5B (lanes 1-9) shows a kinetics experiment with a range of cleavage times. It is clear that the amount of uncleaved protein (~81 kDa, indicated by 'a') decreases while the amount of the cleaved one increases (~57 kDa, indicated by 'b'). Interestingly, after approximately 3 hours, the primary cleavage product of ~57 kDa peptide (indicated by 'b') is further degraded and after 12 hours all His-tagged polypeptides (~81 kDa) completely disappear along with the ~57- and ~37-kDa bands (this was repeated twice more; data not shown). This is corroborated by densitometry depicted in FIGS. 5C and D. The complete disappearance of the FhuA$_{7/10}$-1 and its cleavage products may indicate that a complete digestion of all cleavage sites took place. Such a complete digestion should result in a small 3.6-kDa His$_6$-tagged polypeptide. Such as small protein would be very difficult to detect as it most probably crosses the nitrocellulose paper during blotting. However, when blotting was performed with PVDF, the present inventors were able to detect many more bands (FIG. 5E, lane 2).

Example 4

Permeation Through the Engineered Pore-Forming Polypeptide

In order to use the FhuA$_{7/10}$-1 as part of a safe release mechanism in the nanocarrier, it must maintain a tight seal to prevent leakage of the chemotherapeutic drugs, and it must be cleavable by MMPs. This was tested using electrophysiological recordings.

FhuA$_{7/10}$-1 expressing cells were identified by penning the cells with cobalt-coated beads (FIG. 3). The expressing cells were subjected to electrophysiological experiments at room temperature following the basic protocol of Sunesen et al., 2006 with a few modifications accounting for MMP-7 conditions (Materials & Methods). FIG. 6 shows that throughout a period of ~22 minutes from the time of MMP-7 addition, there is a tight seal with no ionic current, therefore larger molecules such as Doxorubicin cannot leak through in therapeutic applications.

Note that the baseline current started to fluctuate 3 minutes before the very large inward current (t=25 min 45 sec, indicated by 'a' in FIG. 6). This large inward current overwhelmed the amplifier after reaching 20,000 pA (indicated by 'b', where the current trace appears as a straight horizontal line at the bottom of the recording diagram). After 5 seconds the inward ionic current declines, as reflected by the movement of the current trace back, close to the baseline (to point 'c' in the figure). At point 'd', the inward ionic current drastically increases again, passing the maximal measurement capacity of the electrophysiological system. After 16 more seconds, this huge ionic current declines again but much slower than the first decline. This phenomenon of strong current fluctuations alludes to a blocking event of the cleaved β-barrel probably because the beta barrel has not disintegrated completely and parts of the protein, which still remain loosely associated through network interactions, do not enable continuous full opening of the channel.

The gradual decrease of the current of the clamp experiment indicates that the cell did not die but rather recovered, indicating that the ions indeed flow through the damaged channel of the engineered pore-forming polypeptide.

These preliminary results demonstrate the feasibility of designing a pore-forming polypeptide that becomes permeable to ions and possibly to large molecules upon cleavage by MMP-7.

Example 5

OPRD Switch

A new prototypic switch based on the OPRD pseudomonas aregenosa beta barrel channel was also engineered into a nanoswitch. This polypeptide has loops that act as a plug that may be cleaved by MMPs when engineered with a cleavage site.

OPRD was expressed with a non-native signal peptide (surface antigen D15) and a tag was added to the C-terminus of the signal peptide. This native protein does not undergo cleavage by MMP7 when incubated for ~20 hours. Two different MMP T sites, called PL2b and La3 were engineered to be expressed in the OPRD polypeptide.

Results

The native protein (solubilized in DDM) was not cleaved in the presence of MMP-7 (concentration 0.25 Units per 16 ug of total protein).

Example 6

Accessibility of the Crown Loops of OprD to Proteolytic Enzymes

Materials and Methods

Following purification of the protein as in Example 7 below, approximately 1-2 ug of protein were incubated with 0.75 Units (U) enterokinase (Novagen, cat#69066-3) or 0.75 U factor Xa (Novagen, cat#69036-3) or 7.7 U MMP-7 (Cal-Biochem, cat#444270) for various times 0-48 hours as indicated.

Results

Before introducing the matrix metalloproteinase (MMP) cleavage sites into the crown of loops at the top of the OprD, the accessibility of crowning loops to well characterized enzymes, having specific cleavage sites, namely the enterokinase (reK) and the factor Xa (fxa) was assessed.

These enzymes are ubiquitously used for cleaving-off affinity tags from proteins after purification on affinity columns and prior to crystallization. These enzymes (Table 8, below) cleave very specifically and therefore will act as a model for proof of concept.

TABLE 8

| | |
|---|---|
| Enterokinase cleavage site | DDDDK (cleaves after K) |
| Factor Xa | IEGR (cleaves after R) |

Fxa and/or the reK were added to the crowning loops of the OprD and tested for cleavage, the results are shown in FIGS. 7A-C.

As shown in FIGS. 7A-C the crowning loop 8 (L8), was cleaved using the fXa, reK and MMP7. As is shown, all three enzymes were able to successfully cleave the protein, while their respective controls (wild-type protein) lack the corresponding bands.

Example 7

Expression and Purification Protocol

The signal peptide of the native OprD was substituted for that of FadL (SEQ ID NO: 22983) signal sequence to increase the expression in E. coli. The FadL-OprD was tagged at its C-terminus with two glycines and 6 histidines and was subcloned into the petblue2™ vector from Novagen. The DNA was transformed into BL21 (DE3)omp8 a strain of E. coli cells lacking the major outer membrane porins, OmpF, OmpC, OmpA, and LamB. The cells were grown to $OD_{600}$=0.5-0.6 at 37° C., then chilled to 15° C. and induced with 200 uM IPTG and grown overnight. Cells were collected by centrifugation at 4,000 g. The cell pellet was resuspended in TSB buffer (20 mM Tris-HCl pH 8.0, 300 mM NaCl, 10% (v/v) glycerol) then passed through the microfluidizer (Microfluidics M-110S) two to three times (20,000 psi) and centrifuged at 65,000 g for 1 hour. The inner membrane proteins were then solubilized using 0.4% n-Octylpolyoxyethylene (Octyl-POE) in TSB at 37° C. for 2 hours followed by centrifugation at 100,000 g for 1 hour. The inner membrane protein depleted pellet was then solubilized again this time with 3% Octyl-POE and 0.5 mM EDTA in TSB for 2 hours at 37° C. followed by centrifugation at 100,000 g for 1 hour. The soluble fraction was then dialyzed at 4° C. against 0.2% LDAO in TSB overnight and then a second time for 3 hours stirring with a magnet in order to remove the EDTA. The dialyzed soluble fraction was then concentrated on a Ni affinity column (using GE Healthcare Ni Sepharose beads 17-5268-02) and washed with 5 mM Imidazole, 0.5% Octyl-POE, in TSB with final concentration of 0.5M NaCl. The protein was then eluted with 500 mM Imidazole and 0.5% Ocytl POE in TSB. The eluted protein was then dialyzed against 0.5% Octyl POE in TSB to remove the imidazole. Some preparations were then concentrated and dialyzed before cleavage experiments.

Example 8

MMPs Over Expression in Pathologies

The invention described herein, also applies to all of the following diseases since they have an overexpression of MMPs as indicated below.

Rheumatoid arthritis and osteoarthritis—Collagenases especially MMP-2
  collagenases and MMP-2 have been implicated as being related to development of rheumatoid arthritis (Rodriguez-Lopez et al. 2006).
Inflammation and innate immunity—MOSTLY MMP-1 and MMP-7
  MMP-1 for repair of skin wounds and MMP-7 for epithelialization in lung and gut (Pilcher et al. 1997; Dunsmore et al. 1998).
Cancer—MOSTLY MMP2 and MMP9
  Primarily MMP-2 and 9 with tumor invasion and metastasis has now been well established through numerous in vivo studies (Liotta et al. 1980; Stetler-Stevenson 1990).
  (MMP-14) has been proposed as being present in nearly every form of cancer if not the cause of many of the malignant transformations (Golubkov et al. 2005).
  MMP-1, -2, -3, -7, -9, -13 and -14 are overexpressed in colorectal cancers
Angiogenesis—MMP-2, MMP-9 and MMP-14
  has been observed in various diseases characterized by neovascularization. MT1-MMP (MMP-14) and MMP-2 and 9 seem to be predominant MMPs involved with angiogenesis (Bergers et al. 2000; Fang et al. 2000; Galvez et al. 2001; Oh et al. 2004),
Cardiovascular diseases
  MMP-1, -2, -3, and -9 found in the atherosclerotic plaque might be responsible for plaque progression and rupture (Galis et al. 1994).
  MMP-2 overexpression and activity has been shown to induce lower contractility in cardiac tissue (Wang et al. 2006)
Cerebrovascular diseases—MOSTLY MMP2, MMP9
  Not surprisingly, levels of active MMP-2 and 9 are markedly increased during cerebral ischemia (Clark et al. 1997).
  MT-1 MMP, MMP-2 and 9 have been found to be focally present in cerebral aneurysms (Bruno et al. 1998).
  MMP upregulation, especially of MMP-2, -3 and -9, has been observed in intracranial hemorrhage (Fatar et al. 2005).
  MMP-9 is correlated with cerebral edema (Fatar et al. 2005).
  MMP-2 and 9 seem to be involved in different types of dementia (Rosenberg et al. 2001; Adair et al. 2004)
Ocular diseases—MOSTLY MMP-2 and MMP-9
  MMP-2 and -9 are expressed during corneal wound healing as long- and short-term response, respectively (Fini et al. 1992).
Gastrointestinal diseases MOSTLY MMP-1, MMP-3, MMP-7
  High expression of MMP-1 and 3 has been shown in Crohn's disease (Kirkegaard et al. 2004).
  MMP-1, -3, -7, -9, -10, -12 and -14 are overexpressed by different cell types in inflammatory bowel disease (Pender and MacDonald 2004).
  MMP-3 is overexpressed in necrotizing enterocolitis.
  MMP-1 and -3 are increased in peptic and duodenal ulcers (SaarialhoKere et al.1996) while MMP-7 is overexpressed in gastric epithelial cells exposed to *Helicobacter pylori* (Wroblewski et al. 2003)
Oral diseases MOSTLY MMP-8
  Increased presence and activity of collagenases, especially MMP-8, has been known to cause substantial connective tissue destruction leading to periodontitis (Sorsa et al. 2004).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09073990B2). An electronic copy of the "Sequence Listing" will also be available from the USPTO upon request and payment of the fee set forth in 37 CFR 1.19(b)(3).

What is claimed is:

1. An isolated recombinant OprD polypeptide comprising a plugging module and a pore domain, wherein at least one amino acid residue of the amino acid sequence comprising loop 7 as set forth in SEQ ID NO: 22994 is mutated to generate a matrix metalloproteinase (MMP) cleavage site, wherein cleavage of said MMP cleavage site by an MMP enables opening of the pore of said pore domain.

2. The isolated OprD polypeptide of claim 1, wherein said pore domain comprises a β barrel structure.

3. The isolated OprD polypeptide of claim 1, being a monomer.

4. The isolated OprD polypeptide of claim 1, wherein said MMP is selected from the group consisting of MMP-2, MMP-7, MMP-9 and MMP-14.

5. The isolated OprD polypeptide of claim 1, wherein said MMP is MMP-7.

6. The isolated OprD polypeptide of claim 5, wherein said cleavage site comprises the sequence as set forth in SEQ ID NO: 22856.

7. An isolated polynucleotide encoding the isolated pore-forming polypeptide of claim 1.

8. A drug delivery composition, comprising an encapsulating particle and the isolated OprD polypeptide of claim 1.

9. The composition of matter of claim 8, wherein said encapsulating particle is a liposome.

10. A pharmaceutical composition comprising the composition of matter of claim 8.

11. A method of producing a drug delivery composition, comprising inserting the isolated polypeptide of claim 1 into an encapsulating particle, wherein said encapsulating particle comprises at least one lipid layer, and a compartment surrounded by said lipid layer, and further wherein the isolated polypeptide is positioned such that it is capable of forming a pore through said lipid layer in a presence of said protease.

12. A method of treating a disease associated with an up-regulation and/or secretion and/or release of a protease in a subject in need thereof, the method comprising administering to the subject a therapeutically effective amount of the composition of claim 8 to the subject, thereby treating the disease associated with the up-regulation of the protease.

13. The method of claim 12, wherein the disease associated with an up-regulation of a protease is cancer.

14. The method of claim 13, wherein the cancer is a solid tumor.

* * * * *